(12) United States Patent
Mirsky et al.

(10) Patent No.: US 6,326,034 B1
(45) Date of Patent: Dec. 4, 2001

(54) NATURAL EXTRACTED AND SYNTHETIC ANTIOXIDANT COMPOSITIONS

(75) Inventors: Nitsa Mirsky, Nofit; Alona Schachter, Moshav Shefer; Sherbel Sussan, Tarschicha, all of (IL)

(73) Assignee: Natural Compounds LTD, Tivon (IL)

( * ) Notice: Subject to any disclaimer, the term of this patent is extended or adjusted under 35 U.S.C. 154(b) by 0 days.

(21) Appl. No.: 09/469,475

(22) Filed: Dec. 22, 1999

(51) Int. Cl.[7] ................ A61K 35/78; A61K 38/00; A61K 31/44; A61K 31/355; A61K 31/34; A61K 31/07

(52) U.S. Cl. ............... 424/725; 514/2; 514/351; 514/458; 514/474; 514/725

(58) Field of Search ............... 424/725; 514/2, 514/351, 458, 474, 725

(56) References Cited

U.S. PATENT DOCUMENTS 4,976,960 * 12/1990 Grossman et al. ............ 424/195.1
5,145,674 * 9/1992 Lane et al. .................. 424/78.08
5,567,424 * 10/1996 Hastings ..................... 424/195.1

OTHER PUBLICATIONS

The Nutritional Desk Reference, Garrison et al., published 1985 by Keats Publications (CT), pp 61–62.*

* cited by examiner

Primary Examiner—Raymond Henley, III
(74) Attorney, Agent, or Firm—Rashida A. Karmali

(57) ABSTRACT

An antioxidant composition is isolated and purified from natural sources including yeast (*S. carlsbergenesis, S. cerevisiae,* or commercial yeast extract), and saltbush (*Atriplex halimus*), or synthesized chemically, by processes that improve the potency of the product. Compositions containing natural and synthetic compounds, with or without chromium, possessing antioxidant activity are formulated for use in animals and humans. Methods for use of the natural and synthetic antioxidants, alone or in combination with other antioxidant agents, for regulating oxidative conditions are presented.

9 Claims, 27 Drawing Sheets

NATURAL EXTRACTED AND SYNTHETIC ANTIOXIDANT COMPOSITIONS

Figure 1:
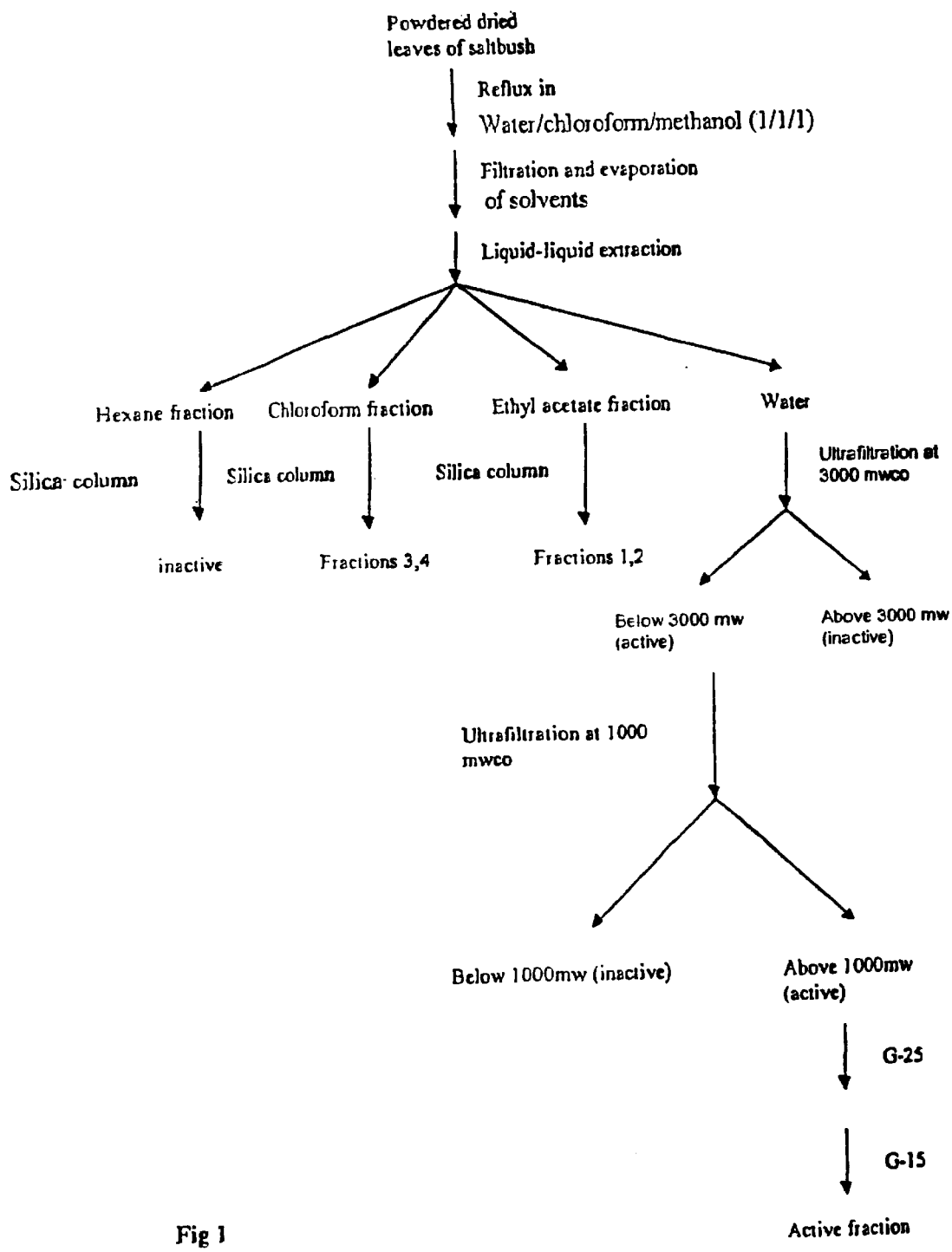

The present invention is directed to processes of isolating purified compositions with or without chromium from a variety of natural sources including, but not limited to, a yeast strain *S. carlsbergensis, S. cereveisiae* or any commercial yeast extract, or a Saltbush, *Atriplex halimus,* growing in the Mediterranean area. The invention also comprises synthetic sources of chromium, or chromium salts including, but not limited to $CrCl_3$, chromium sulfate, chromium gluconate, chromium-cysteine, chromium-glutathione, chromium-N-acetyl cysteine or chromium tartarate. The invention is also directed to formulations of the antioxidants, with or without chromium, which specifically regulate glucose and lipid metabolism, and insulin and antioxidant activities in mammals at enhanced risk for, or having, a diabetic condition, cardiovascular diseases and hyperlipidemia. In the practice of the method of treating diabetes, compositions containing the chromium containing antioxidants are used to regulate the diabetes related metabolic disregulation without general cytotoxic effects.

1. BACKGROUND OF THE INVENTION

Chromium (Cr) has been known as an essential trace element in animal and human nutrition. Cr deficiency may result in various symptoms including increased concentrations of circulating insulin, elevated blood glucose and cholesterol, decreased insulin receptor number, elevated triglyceride and free fatty acid levels and reduced high-density lipoprotein (HDL) cholesterol levels. Chromium levels in most organs decline with age and in diabetics its levels are even lower-than in healthy adults. Anderson, R. A., Clin. Physiol. Biochem. 4: 31–41 (1986).

Chromium deficiency may also produce hypercholesterolemia. The intake of dietary chromium probably varies considerably. In United States, it probably averages 60–90 mg/day with 20–60% of individuals tested consuming below the proposed recommendation of 50–200 mg/day. Refinement of whole grains removes most of the chromium and it has been proposed that chromium deficiency in the developed world is partly because of the reliance on refined and processed food products.

Inorganic Chromium Salts, are absorbed very poorly (about 1%). In biologic systems, chromium is found primarily in the +3 ionic state, although the +2 and +6 states also occur.

The present invention relates to compositions of natural extracted with or without chromium and synthetic antioxidant chromium compounds, for application to individuals to inhibit oxidative injury within the target cells. In the practice of the invention, the natural and synthetic antioxidant compounds, can be applied to supplement traditional pharmaceutical, hormonal and/or nutritional therapies for various diseases.

2. SUMMARY OF INVENTION

In accordance with the invention, processes of isolating from natural sources, compositions of natural antioxidants are provided for the production of improved and more purified compositions. The natural sources used include, but are not limited to the yeast strains *S. carlsbergensis, S. cerevisiae* and commercial yeast extract, and the saltbush *Atriplex halimus* growing in the Mediterranean.

The present invention also provides chromium salts and synthetic sources of chromium complexes, including, but not limited to chromium chloride, chromium gluconate, chromium sulfate, chromium-cysteine, chromium-glutathione, chromium-N-acetyl cysteine or chromium tartarate.

The present invention provides formulations of natural and synthetic compositions for application in a variety of diseases or abnormal conditions including, hyperlipidemia, hypercholesterolemia, obesity, vascular and fibrotic proliferative diseases, cancer, skin warts, skin lesions, UV-induced skin damage, diabetes and diabetic complications or to regulate abnormal metabolic processes.

The present invention provides formulations of natural and synthetic antioxidants with or without chromium, which can be applied in combination with an effective amount of one or more additional antioxidants including vitamin C, vitamin E, reduced glutathione, manganese, beta-carotene, ergothioneine, zinc, selenium, cysteine, N-acetyl cysteine, methionine or 2-mercaptoethanol.

According to an additional aspect of the present invention, there is provided a method to regulate lipid peroxidation, lipid oxidation and metabolism and antioxidant activities by applying formulations of an effective amount of natural with or without chromium and/or synthetic chromium compositions.

According to yet another aspect of the invention, there is provided a method to regulate hyperlipidemia, hypercholesterolemia, obesity, vascular and fibrotic proliferative diseases, cancer, skin warts, skin lesions, UV-induced skin damage, diabetic neuropathy or to regulate lipid metabolism and antioxidant activities by applying formulations of natural and/or synthetic compositions with or without chromium containing compounds, in combination with an effective amount of one or more antioxidants including vitamin C, vitamin E, reduced glutathione, manganese, beta-carotene, ergothioneine, zinc, selenium, cysteine, N-acetyl cysteine, methionine or 2-mercaptoethanol.

The present invention also provides a method to regulate lipid peroxidation, free radical generation, lipid metabolism and antioxidant activities, including application of formulations of natural and/or synthetic compositions with or without chromium in combination with a conventional therapeutic regimen including hormonal therapy or one or more pharmaceutical agents.

The present invention is based on the discovery of improved process to produce more purified compositions of natural and/or synthetic antioxidants with or without chromium.

The present invention is based on the discovery of improved processes to produce synthetic compositions of chromium complexes.

The present invention is also based on the discovery of improved formulations of natural and/or synthetic compositions with or without chromium containing compounds, which exhibit a greater potency in regulating metabolic abnormalities associated with generation of or failure in removal of oxygen free radicals.

It is also the object of the present invention to provide formulations of natural and/or synthetic compositions with or without chromium containing compounds, which are effective when used alone or in combination with antioxidants or conventional therapies.

It is another object of the present invention to provide methods for prevention and treatment of inflammatory diseases, specifically abnormalities in oxygen radicals and lipid metabolism, arachidonic acid metabolism, cyclooxygenase activity or antioxidant activities.

Still other objects and advantages of the invention will in part be obvious and will in part be apparent from the specification.

The invention accordingly comprises the several steps and the relation of one or more of such steps with respect to each of the others, and the product embodying properties, which are adapted to effect such steps and methods, all as exemplified in the following detailed disclosure, and the scope of the invention will be indicated in the claims.

3. BRIEF DESCRIPTION OF THE DRAWINGS

For a fuller understanding of the invention, reference is had to the following description taken in connection with the accompanying drawings, in which:

FIG. 1 is a diagram illustrating the individual steps in the process by which the natural compositions with or without chromium containing compounds are extracted and purified from the saltbush. These steps include: a) Extraction of powdered dry leaves in water:methanol:chloroform 1:1:1 respectively, filtration and evaporation of solvents. The crude extract was dissolved in water, and fractionated in liquid—liquid extraction with n-Hexane, chloroform and ethyl acetate. The aqueous fraction was filtered through size exclusion membranes, followed by gel filtration columns. The organic fraction was further purified by silica columns.

Figure 2:
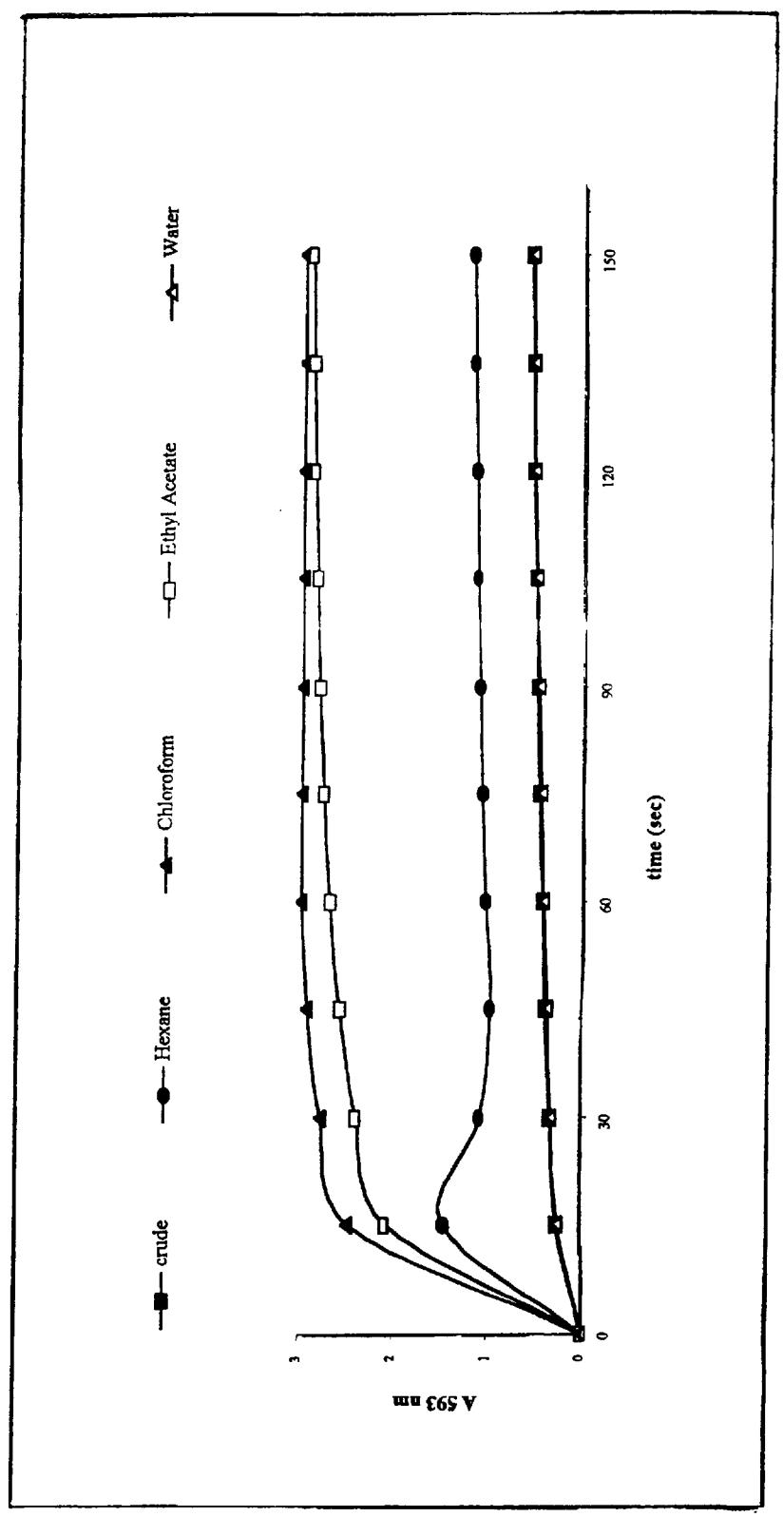

FIG. 2 describes antioxidant activity of fractions extracted from the saltbush by different solvents.

Figure 3:
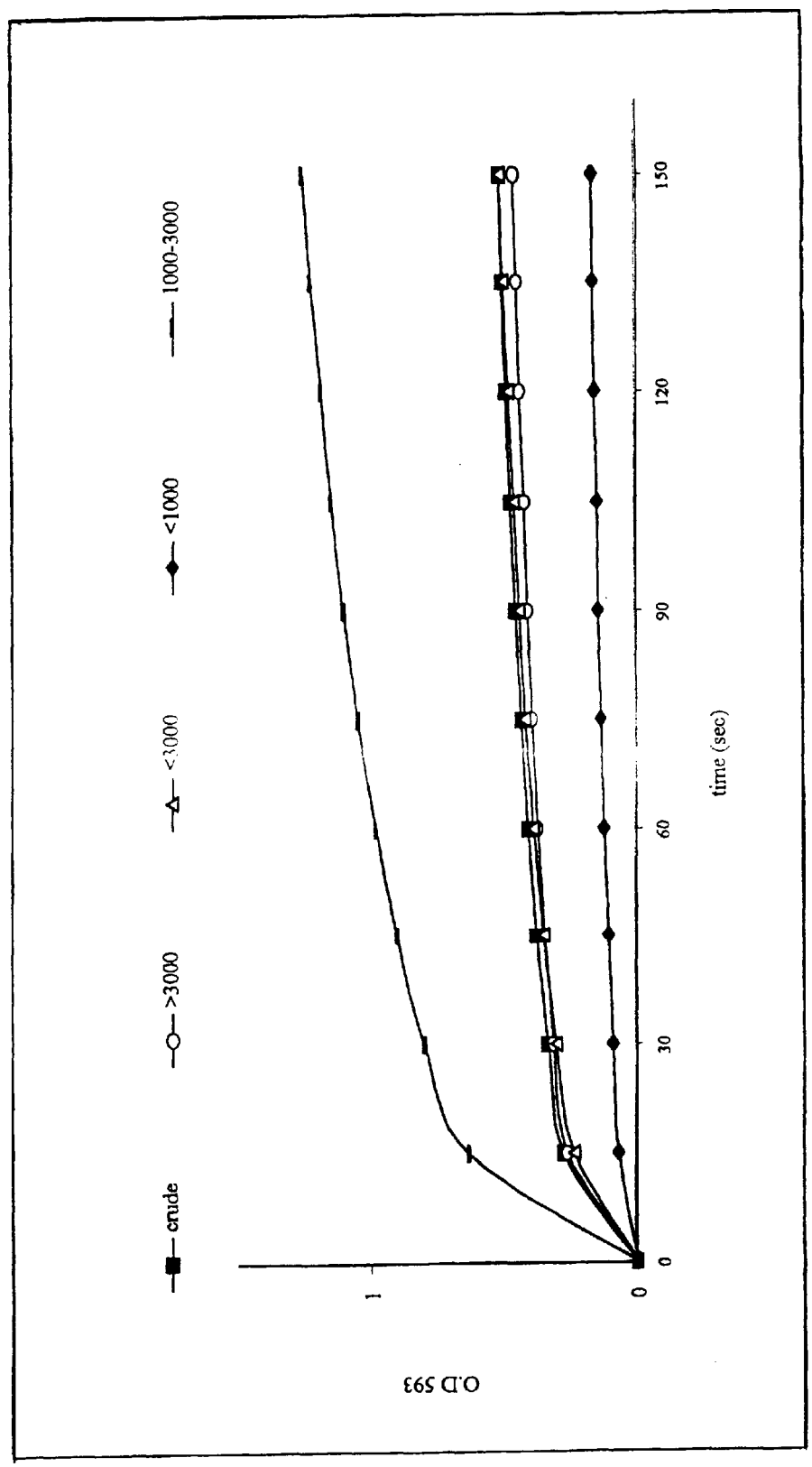

FIG. 3 Describes antioxidant activity in vitro measured in the FRAP assay, in aqueous fractions isolated from the saltbush, using size exclusion membranes.

Figure 4:
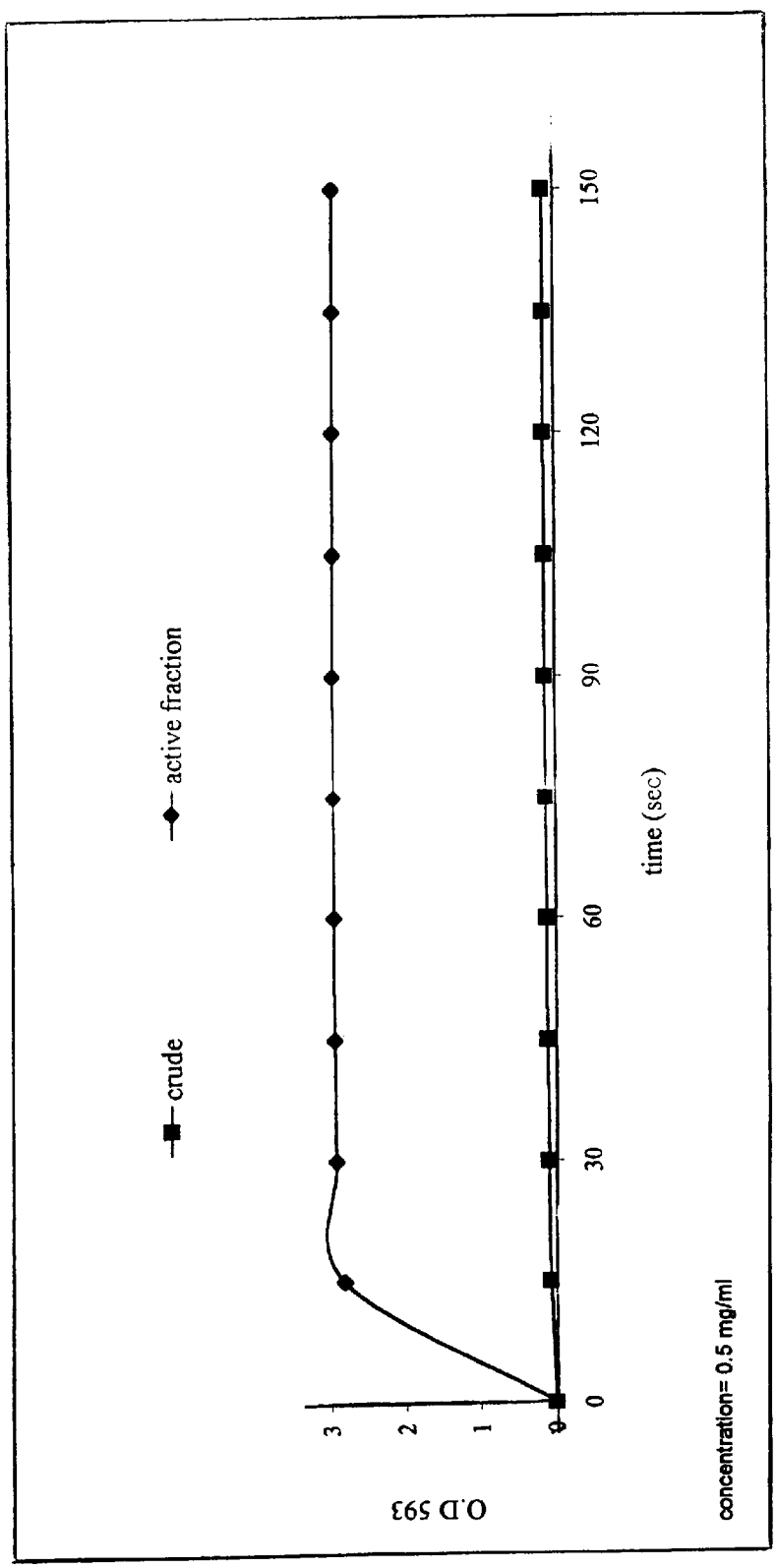

FIG. 4 Describes antioxidant activity in vitro measured in the FRAP assay, in the aqueous fractions isolated from saltbush, eluted from sephadex G-25, G-15 and silica gel columns. The antioxidant activity of the active fraction is compared to the activity of the crude extract.

Figure 5:
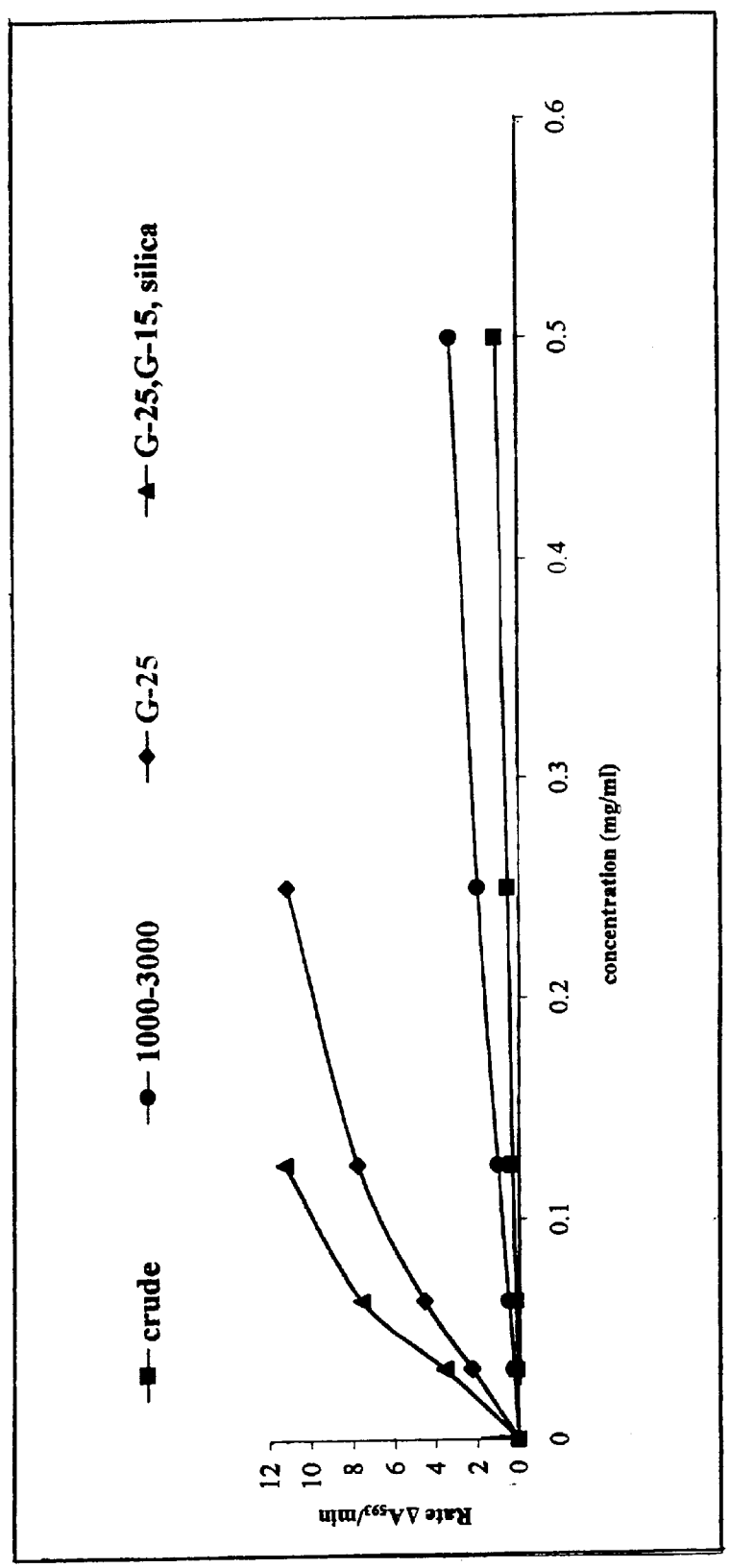

FIG. 5 Describes the results of the dose response studies of antioxidant activity measured in the RFAP assay in vitro, for different purification steps of the aqueous fraction crude filtrate from size exclusion membranes (1000–3000 cutoff), and eluate from sephadex G-25, G-15 and silica.

Figure 6:
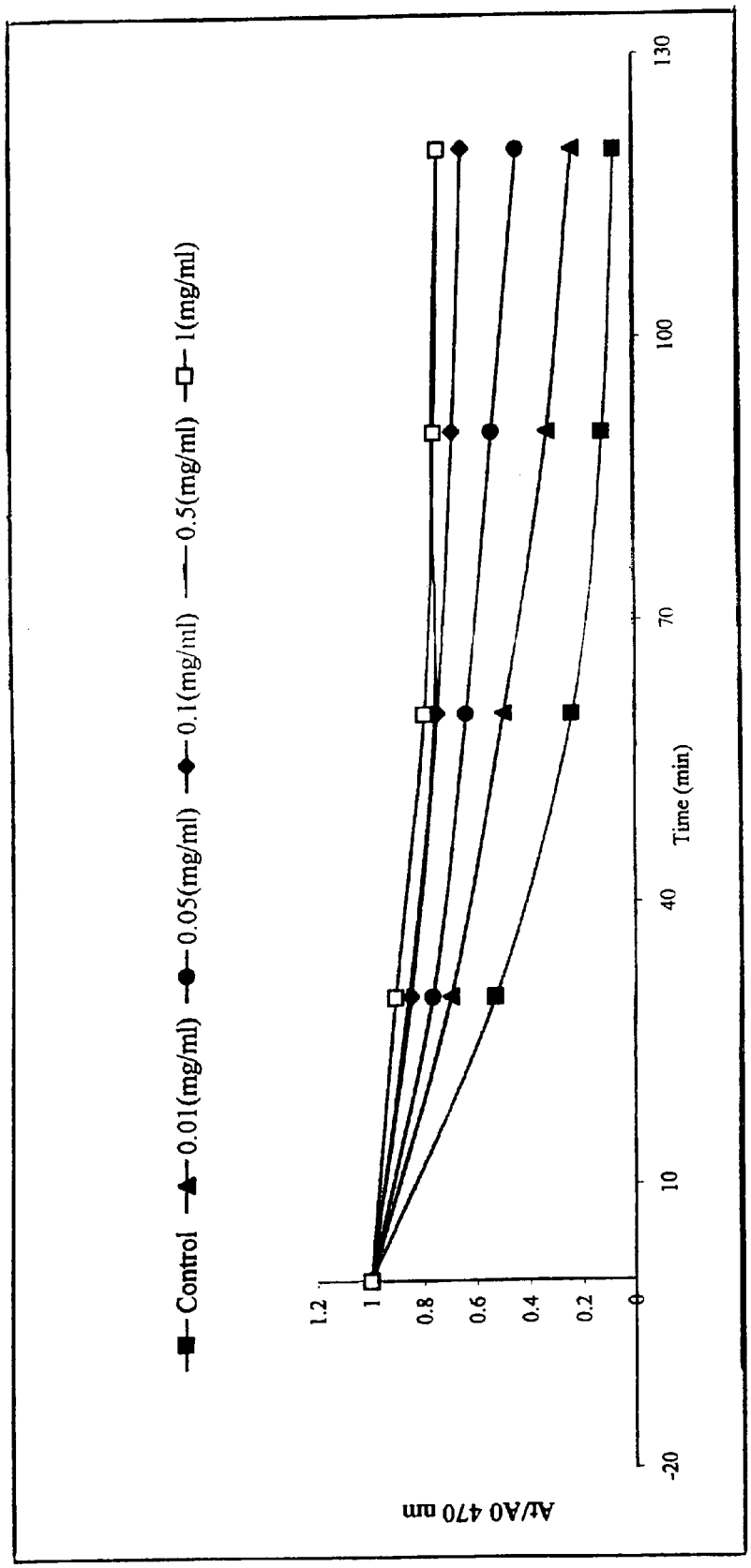

FIG. 6 Describes the results of dose response study of antioxidant activity measured in the beta-carotene test in vitro for the aqueous fraction isolated from saltbush, and purified by filtration and elution from G-25 column.

Beta-carotene and linoleic acid emulsion were incubated at 50° C. in the absence (control) or the presence of different concentrations of the aqueous fractions. The changes in beta-carotene absorbance at 470 nm in 30 minutes intervals were measured.

Figure 7:
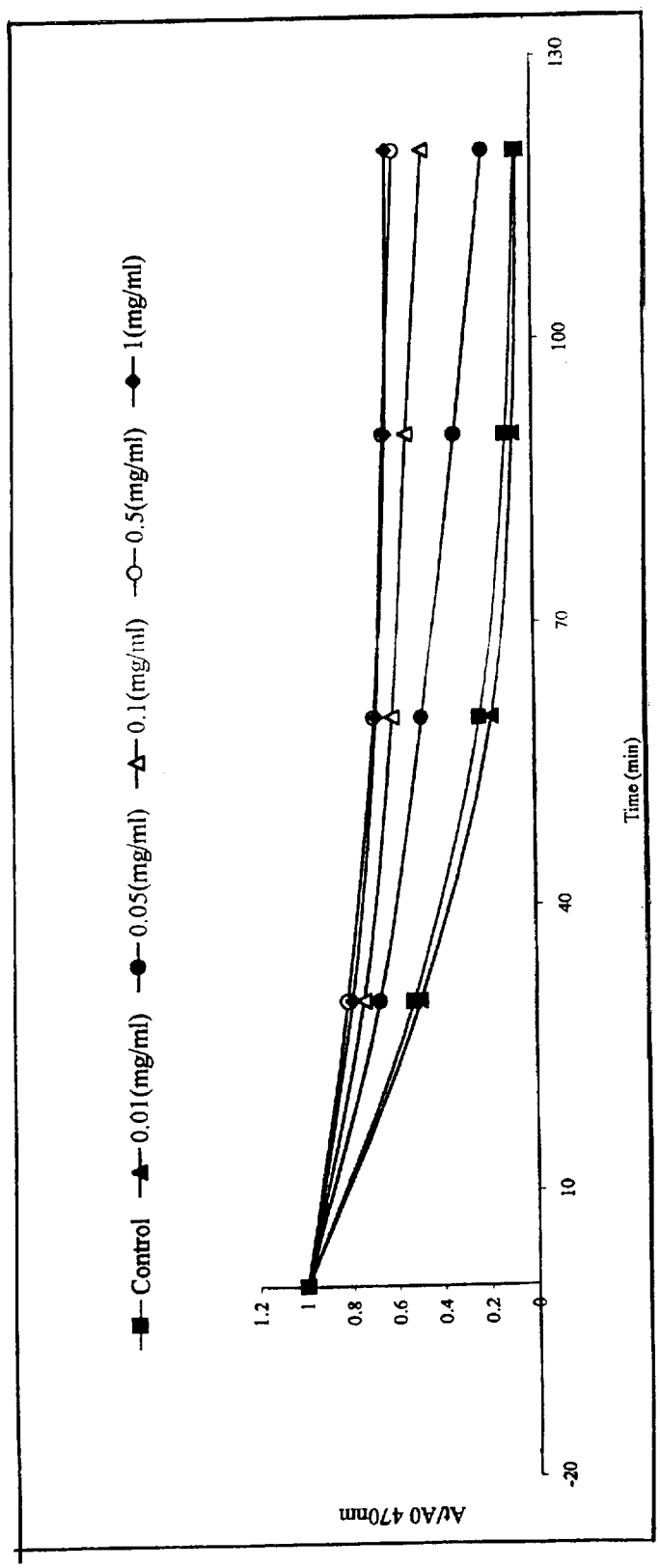

FIG. 7 Describes the results of dose response study of antioxidant activity measured in the beta-carotene test in vitro for the crude aqueous fraction isolated from saltbush.

Figure 8:
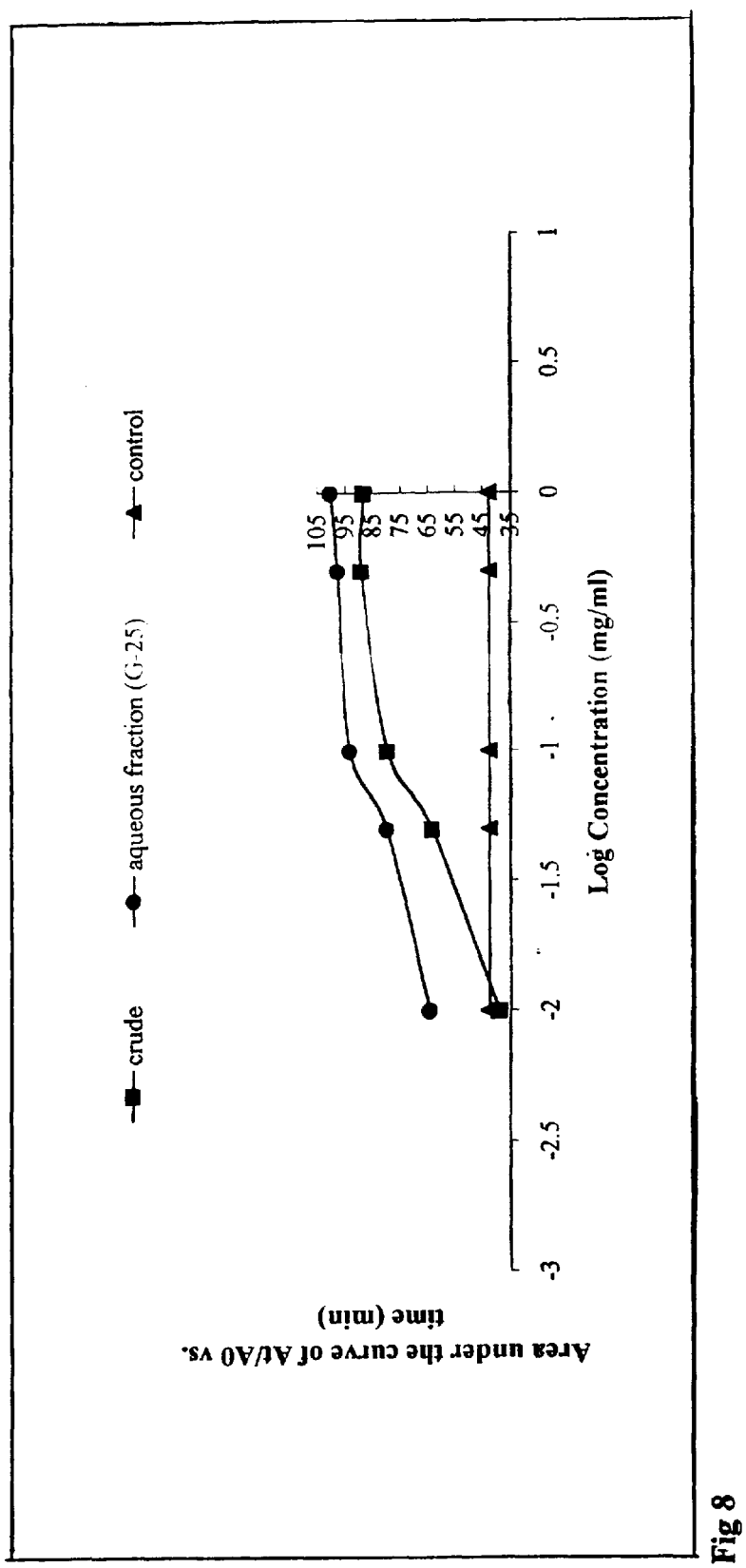

FIG. 8 Describes dose response enhancement of antioxidant activity of the crude aqueous fraction isolated from saltbush, and the fraction eluted from G-25 column. The relative activity is presented according the area under the curve (AUC) from FIGS. 6 and 7.

Figure 9:
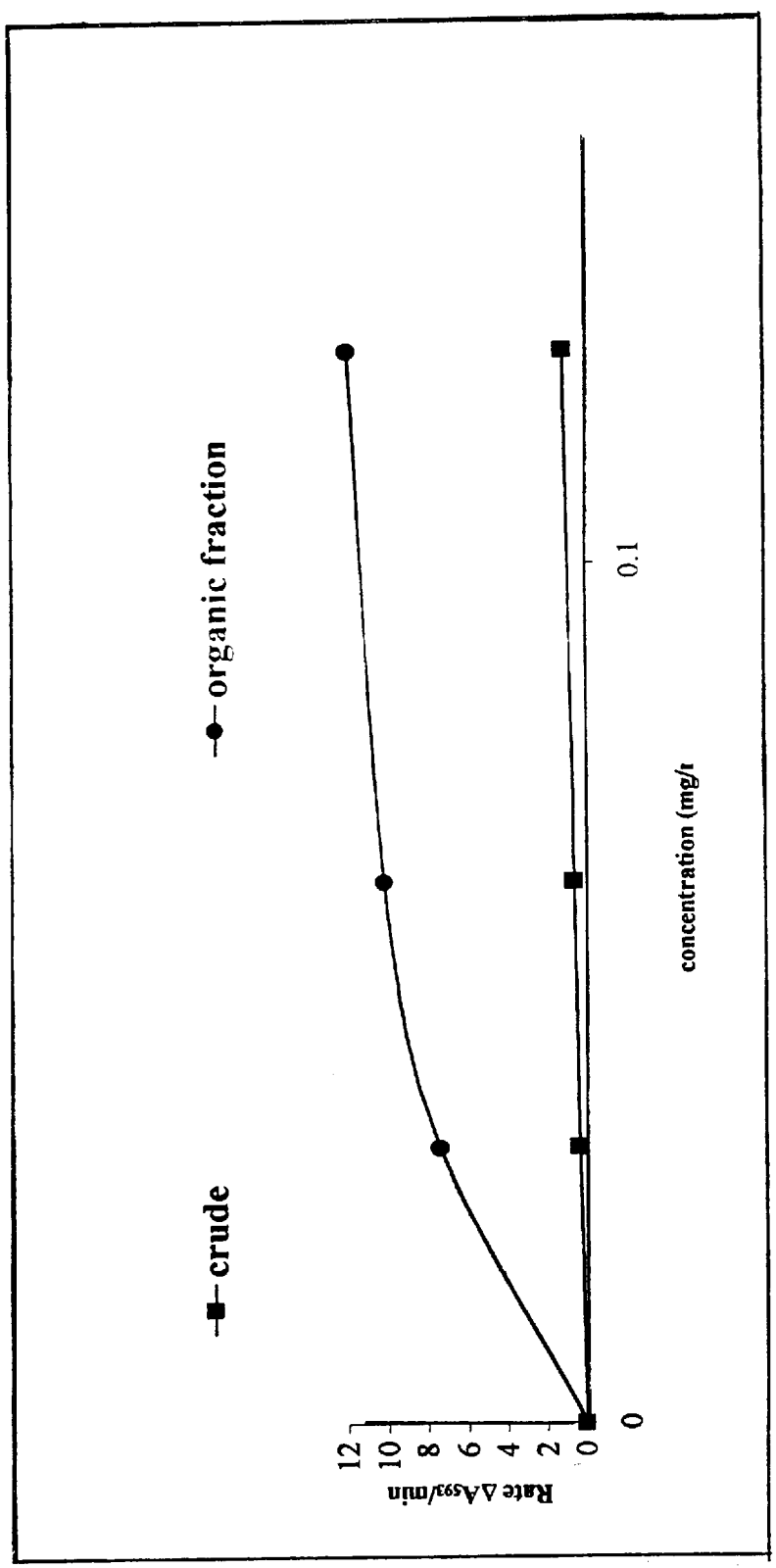

FIG. 9 Describes antioxidat activity in vitro measured in the FRAP assay for organic fraction extracted from the saltbush by chloroform, and eluted from silica gel column by acetone (Fraction 3).

Figure 10:
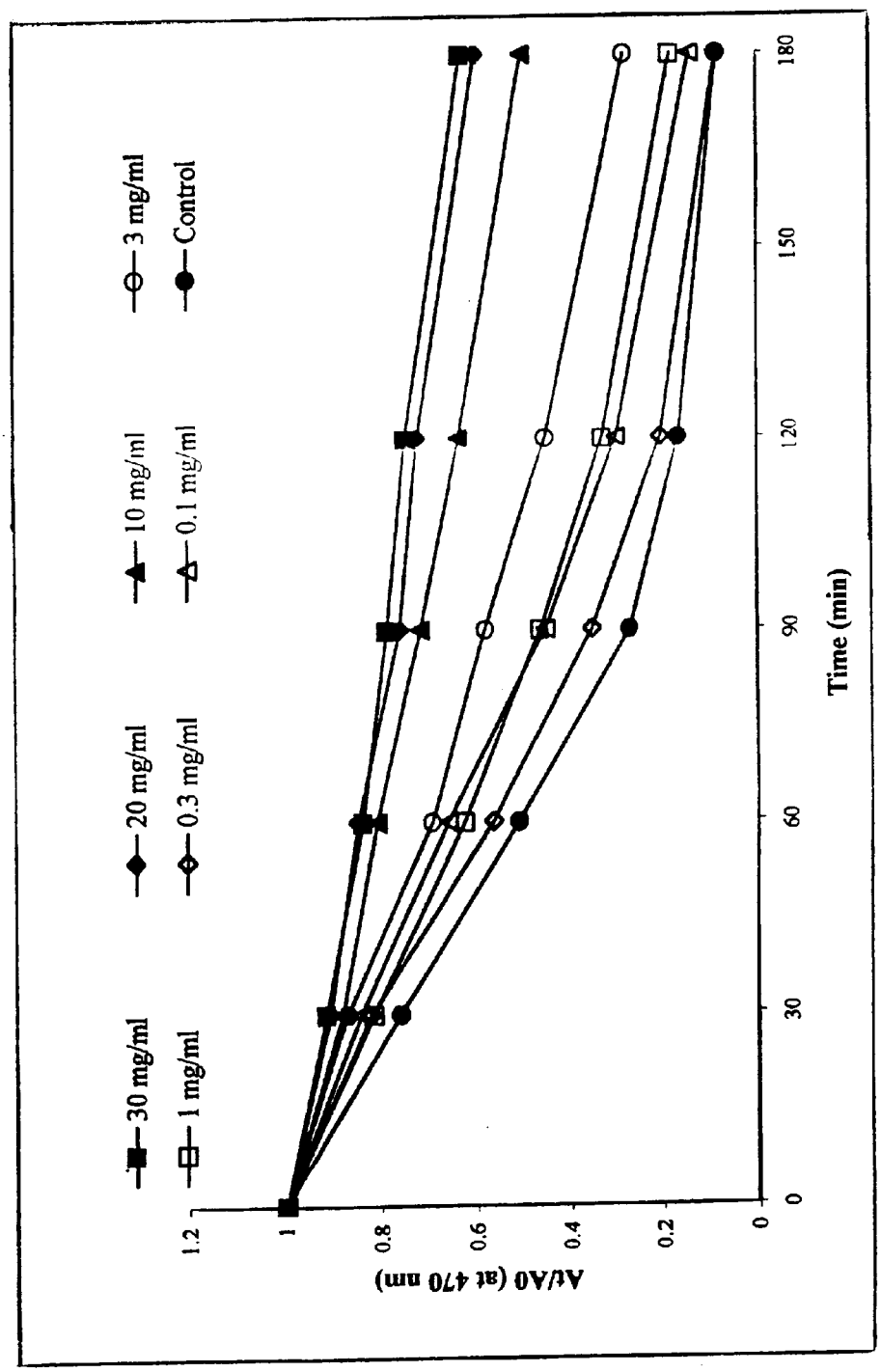

FIG. 10 Describes the results of dose response activity measured in beta-carotene test in vitro for the aqueous fraction isolated from yeast extract, and purified by filtration and elution from G-25 column.

Figure 11:
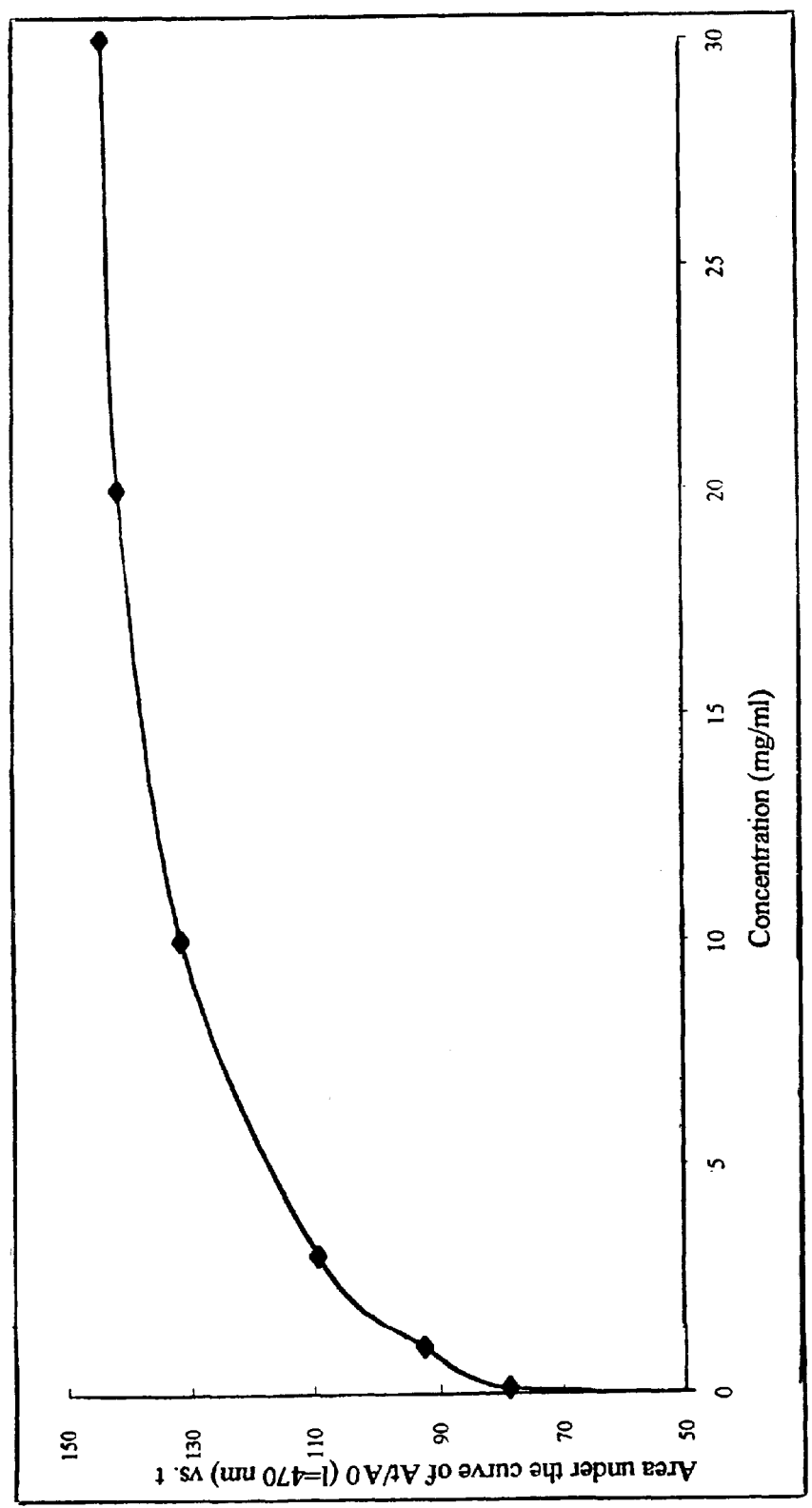

FIG. 11 Describes the dose response curve for antioxidant activity of the aqueous fraction extracted from yeast. Area under the curve for every dose examined was calculated according to FIG. 10.

Figure 12:
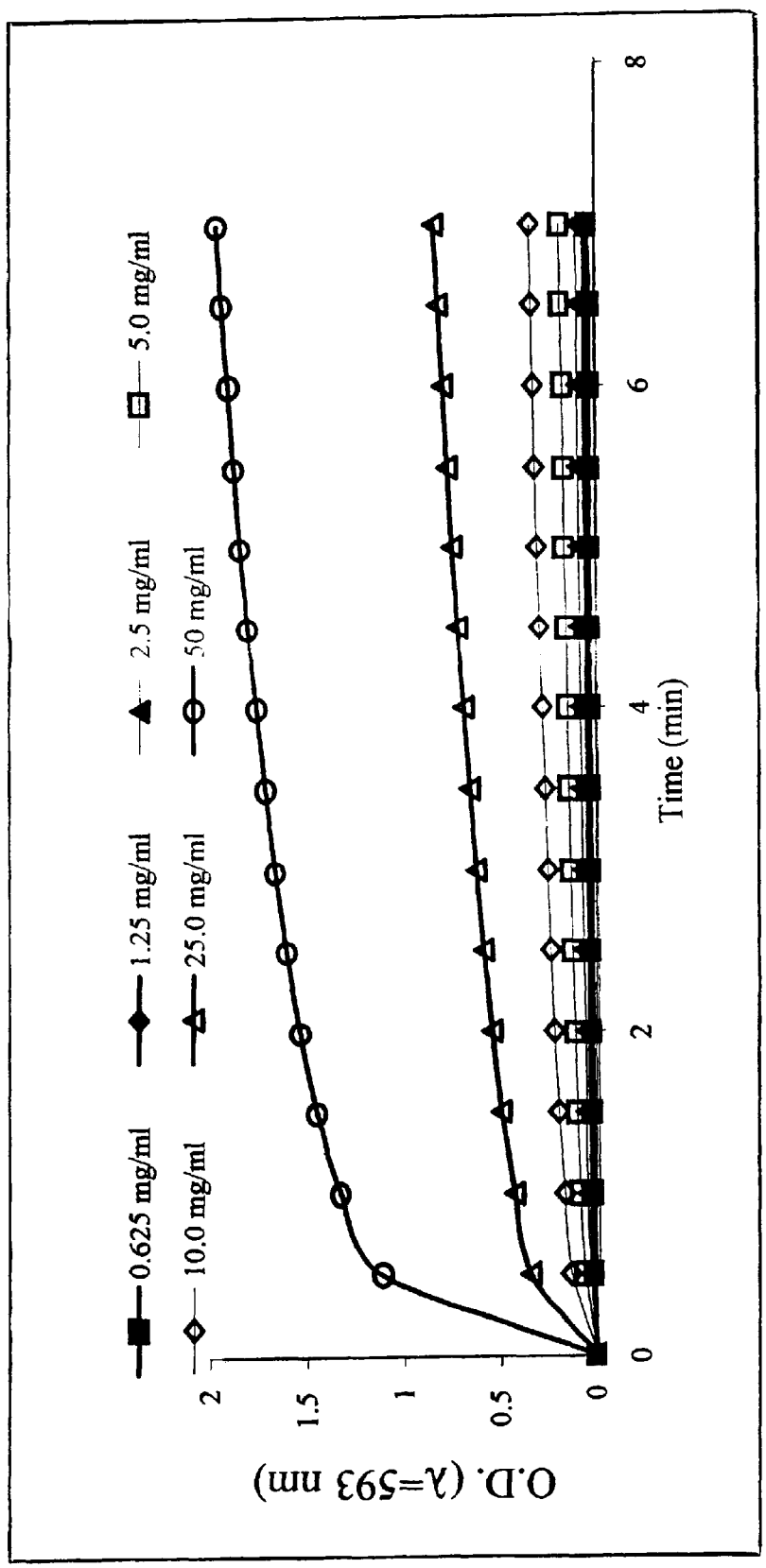

FIG. 12 Describes the antioxidant activity in vitro in the FRAP assay of crude yeast extract, in different concentrations measured.

Figure 13:
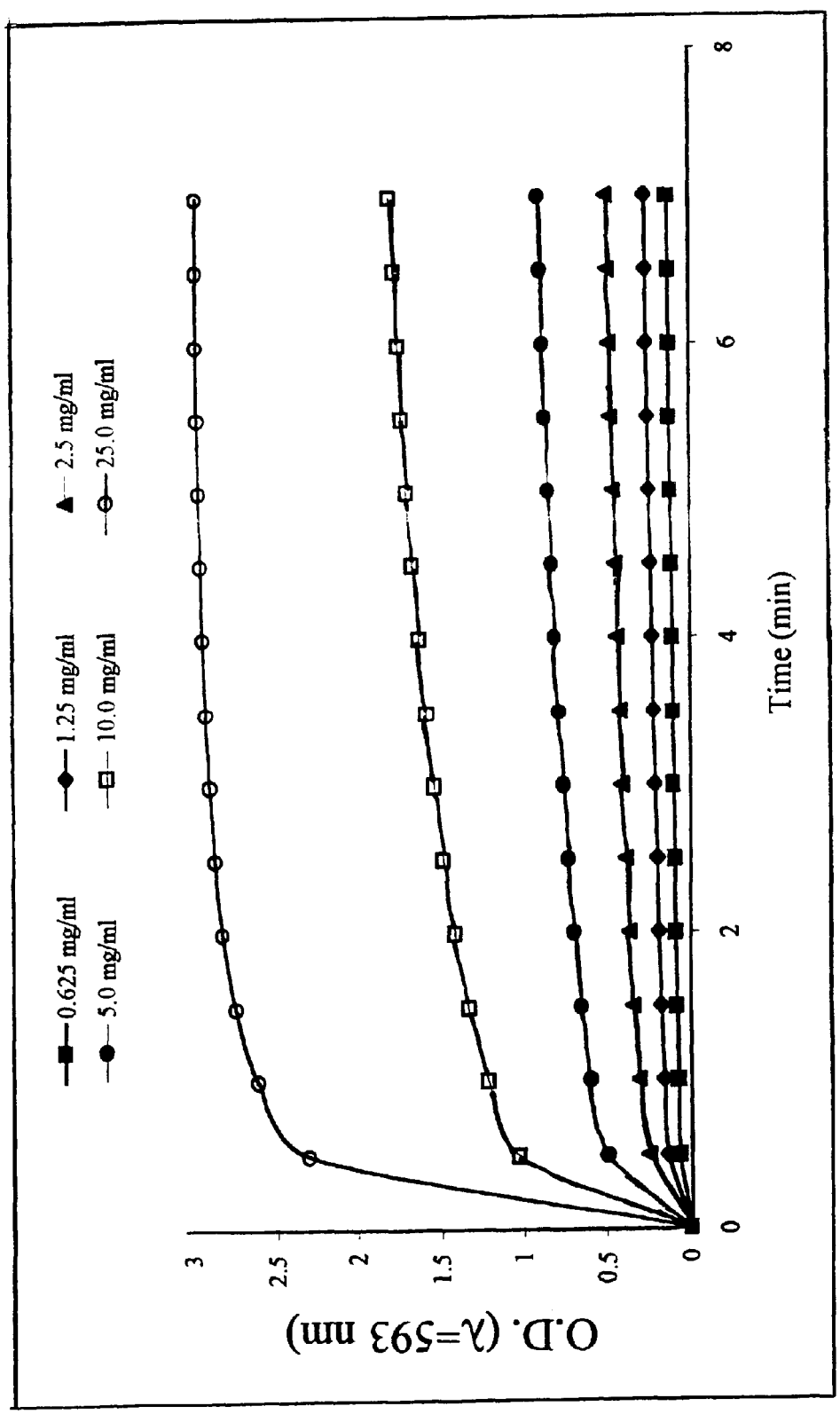

FIG. 13 Describes the antioxidant activity in vitro in the FRAP assay of chloroform fraction extracted from yeast extract, in different concentrations measured.

Figure 14:
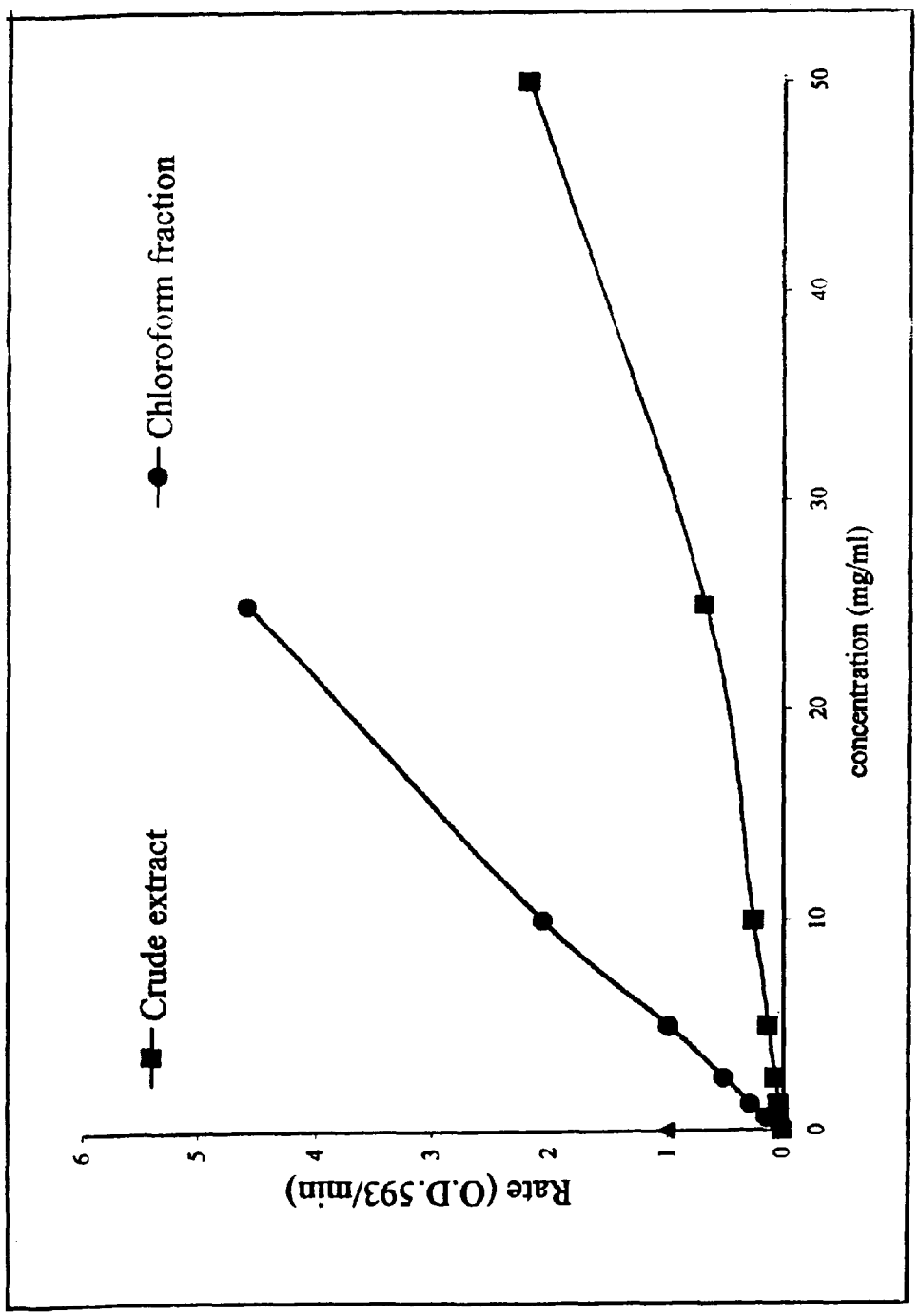

FIG. 14 Describes dose dependent antioxidant activity in vitro in the FRAP assay in the chloroform fraction extracted from yeast compared to the crude extract.

Figure 15:
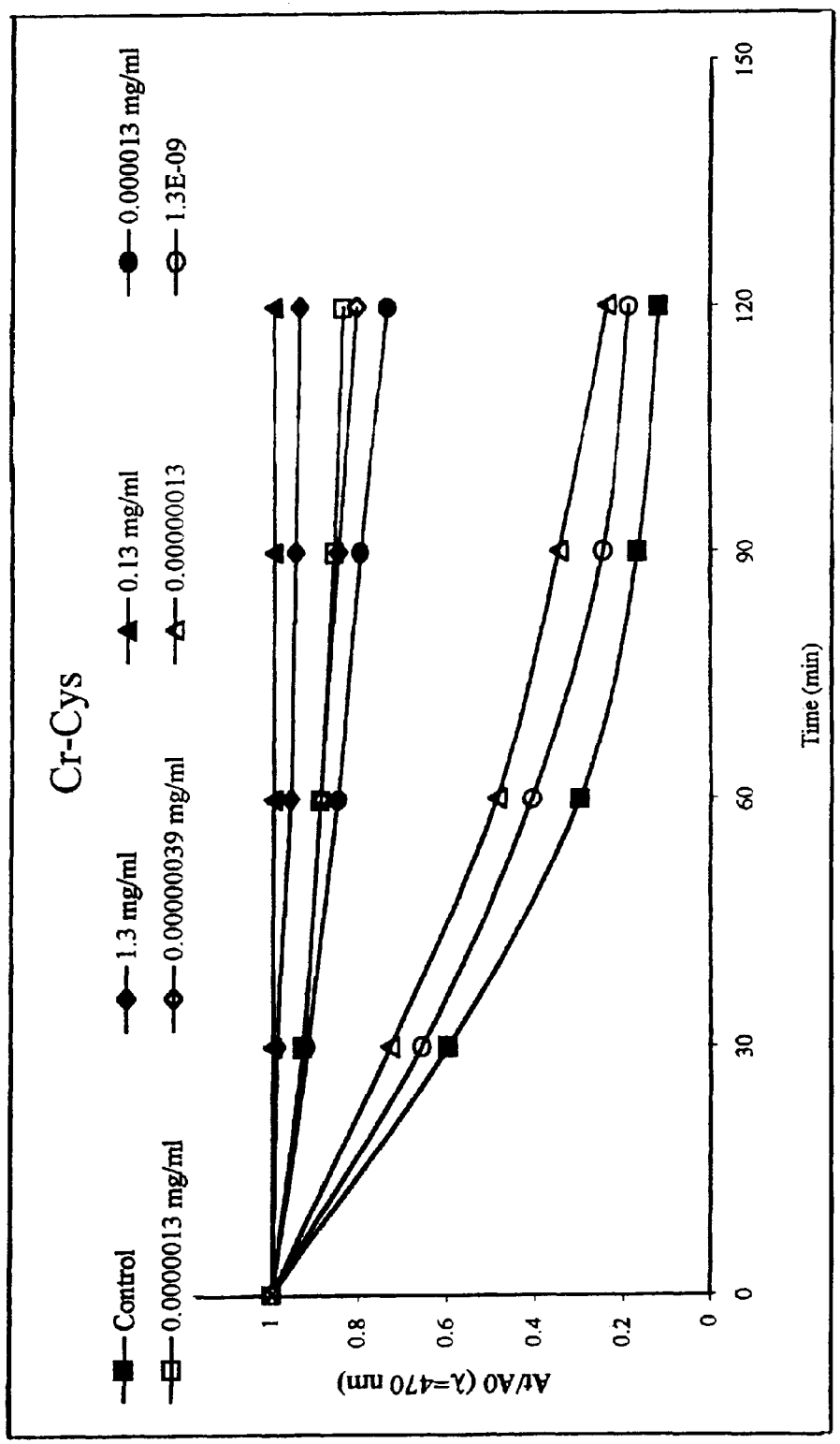

FIG. 15 Describes the results of dose response study of antioxidant activity measured in the beta-carotene test in vitro, for chromium cysteine complex (Cr-Cys). (concentrations written according to chromium concentrations in the complex).

Figure 16:
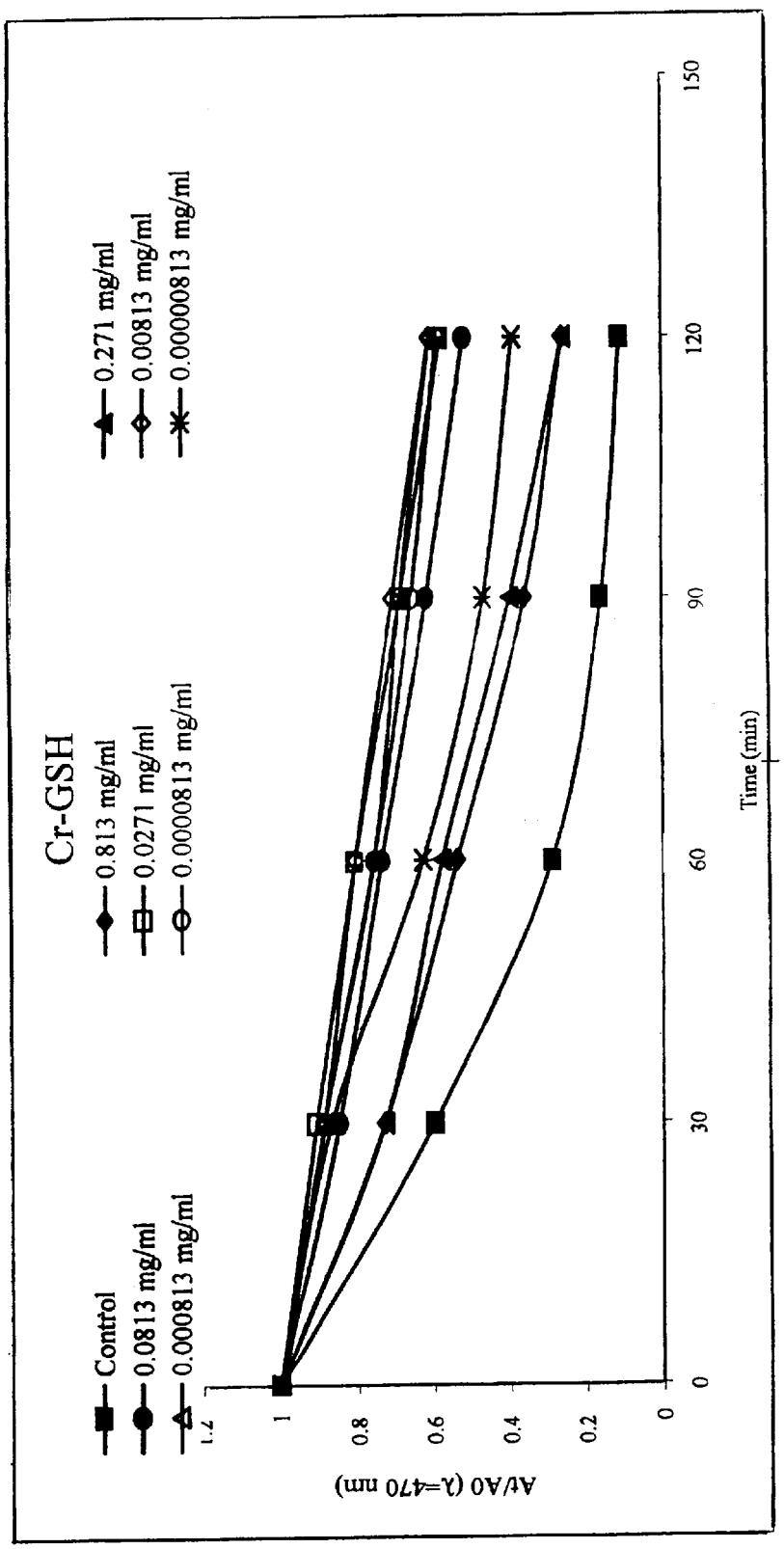

FIG. 16 Describes the results of dose response study of antioxidant activity measured in the beta-carotene test in vitro, for chromium glutathione complex (Cr-GSH). (concentrations written according to chromium concentrations in the complex).

Figure 17:
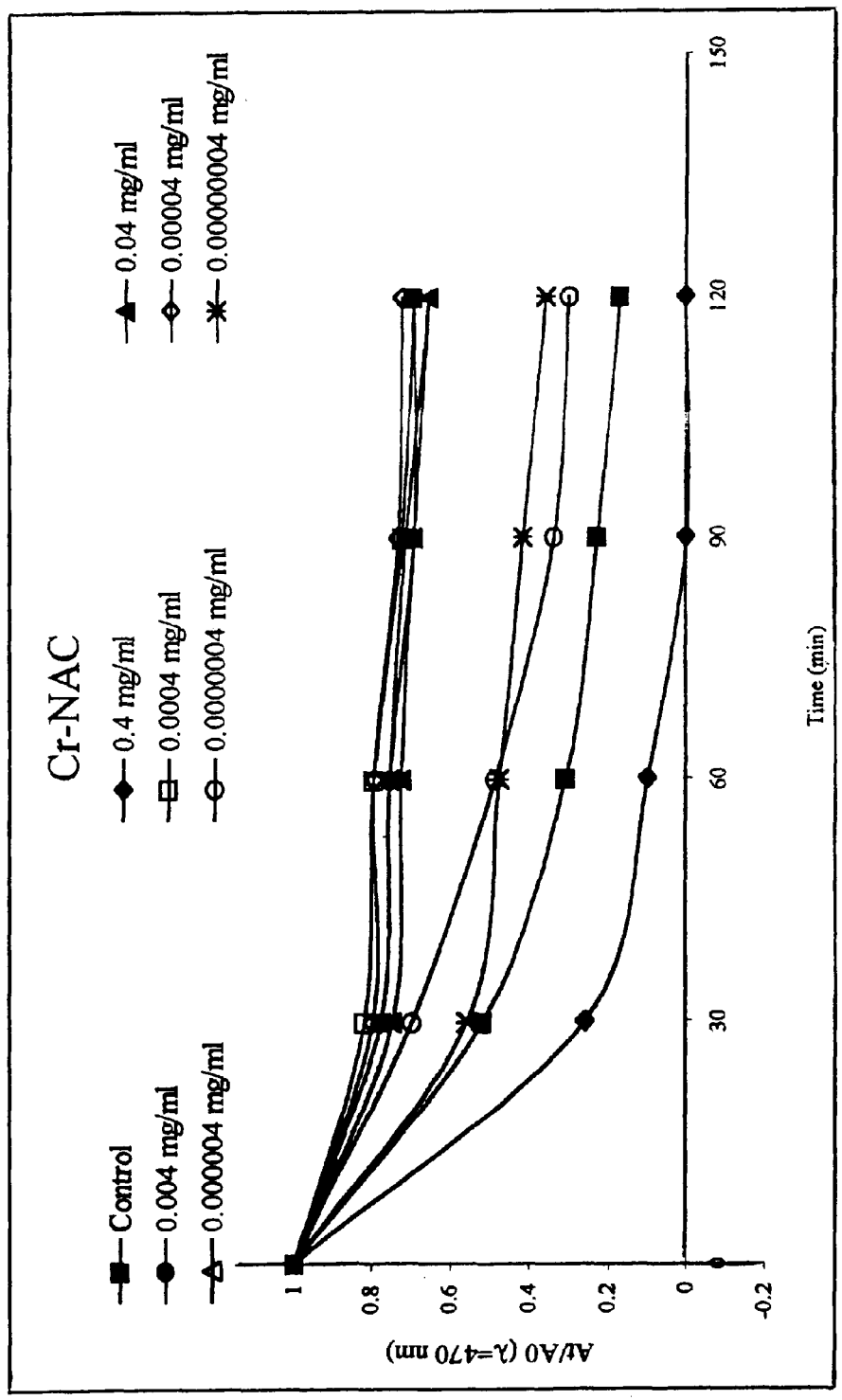

FIG. 17 Describes the results of dose response study of antioxidant activity measured in the beta-carotene test in vitro, for chromium N-acetyl cysteine complex (Cr-NAC). (concentrations written according to chromium concentrations in the complex).

Figure 18:
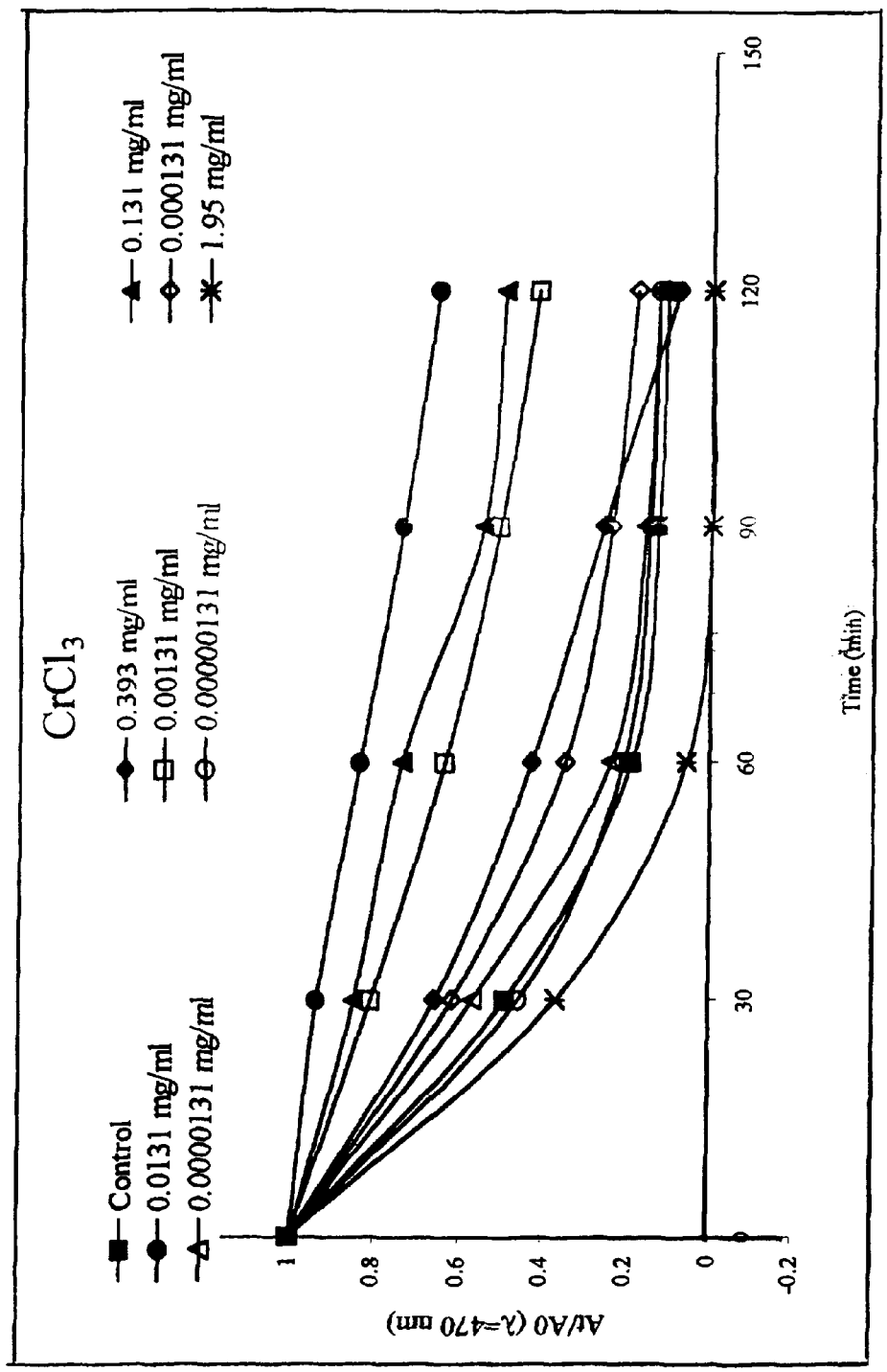

FIG. 18 Describes the results of dose response study of antioxidant activity measured in the beta-carotene test in vitro, for chromium chloride ($CrCl_3$). (concentrations written according to chromium concentrations in the compound).

Figure 19:
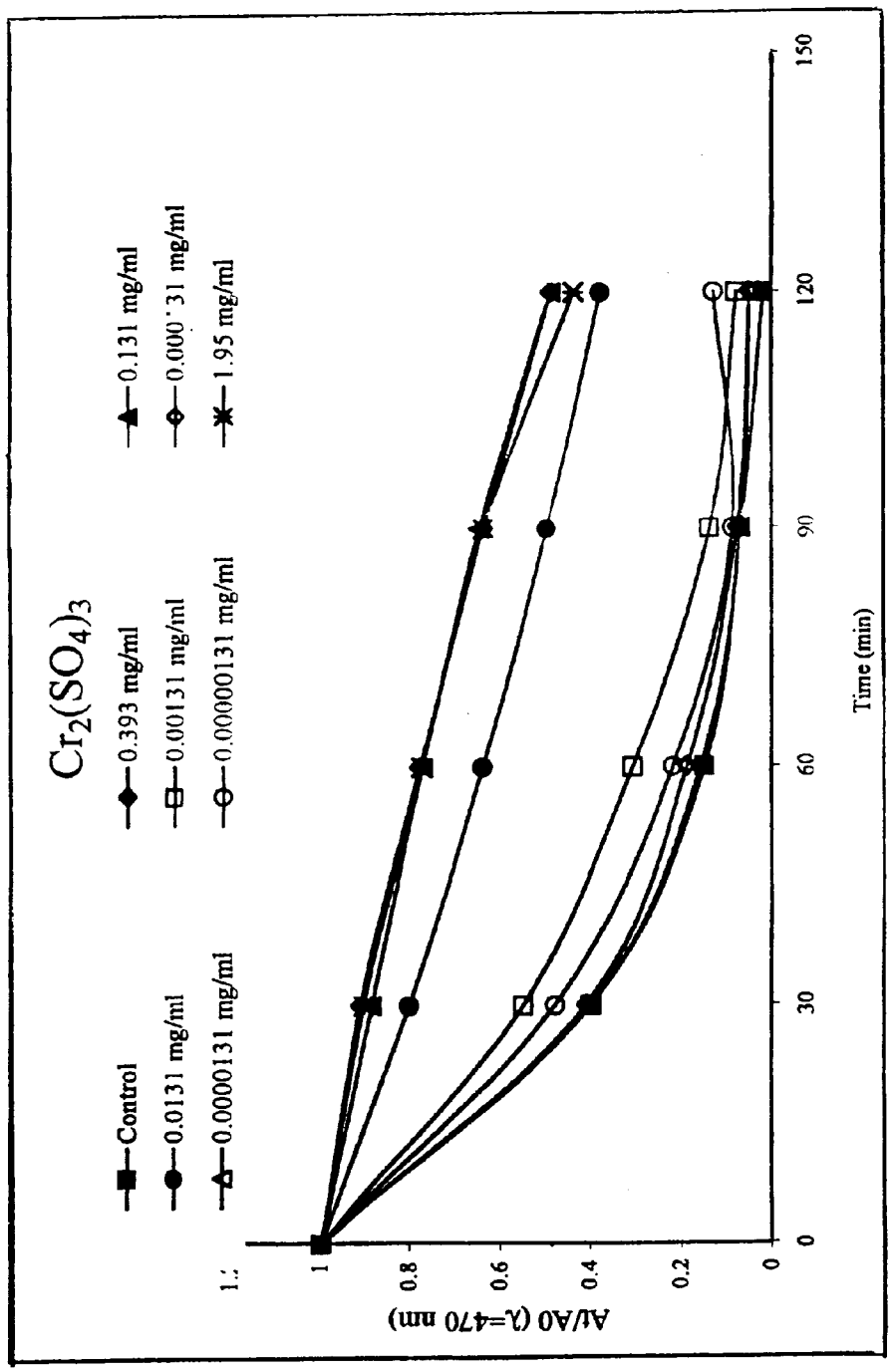

FIG. 19 Describes the results of dose response study of antioxidant activity measured in the beta-carotene test in vitro, for chromium sulfate [$Cr_2(SO_4)_3$]. (concentrations written according to chromium concentrations in the compound).

Figure 20:
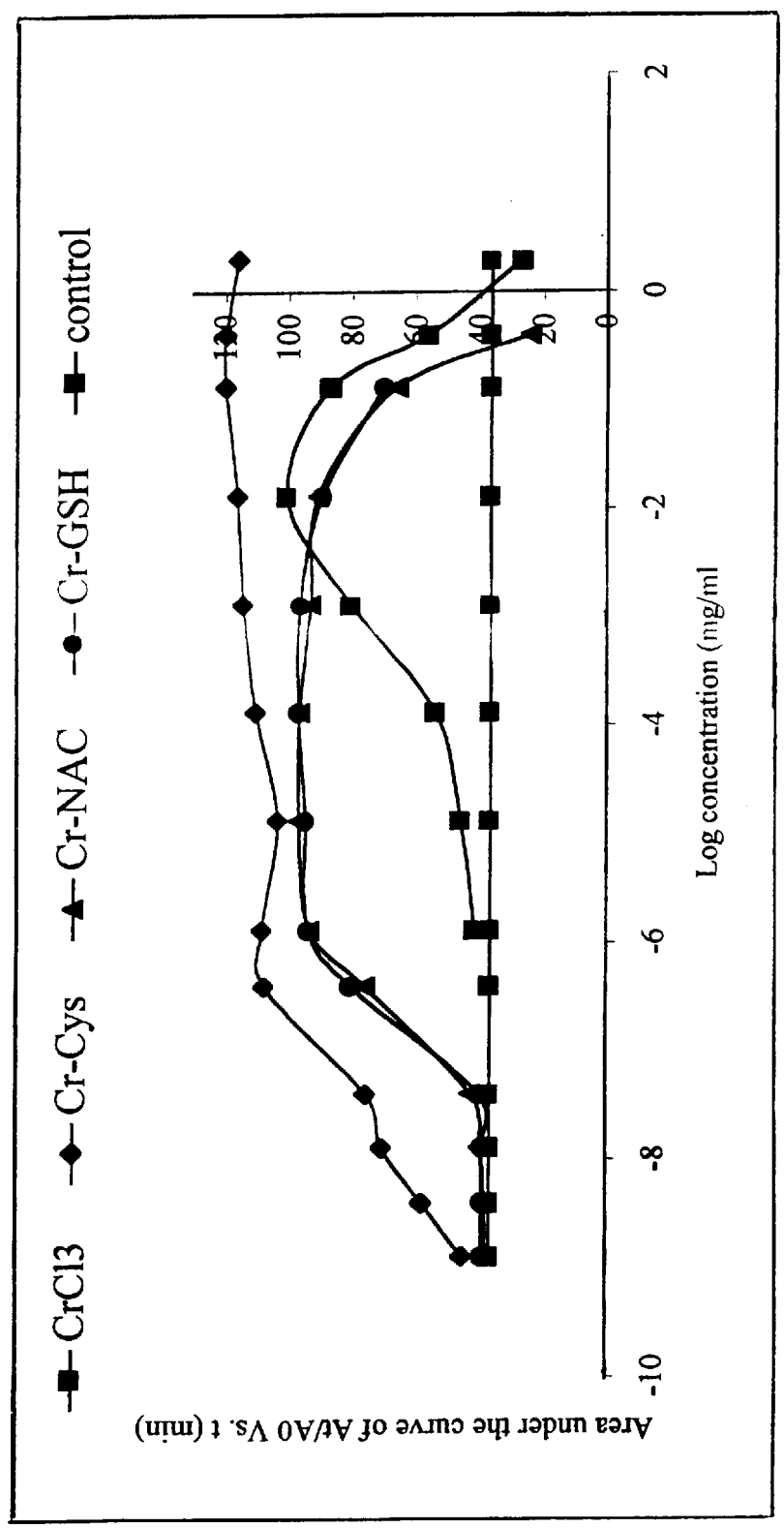

FIG. 20 Describes dose response enhancement of antioxidant activity in the beta-carotene test of several chromium complexes, presented according to area under the curve calculated from FIGS. 15–18.

Figure 21:
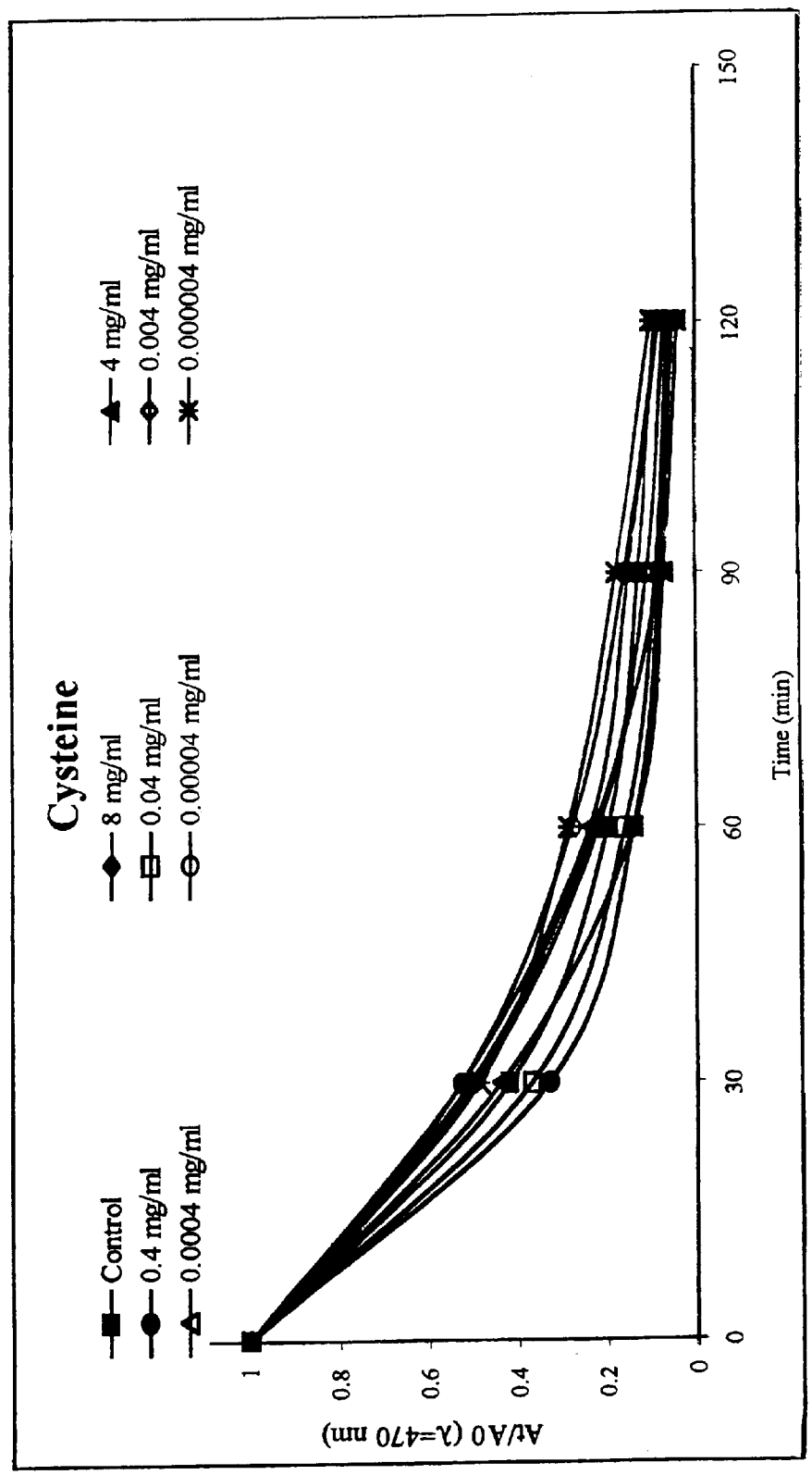

FIG. 21 Describes the results of dose response study of antioxidant activity measured in the beta-carotene test in vitro, for cysteine (Cys).

Figure 22:
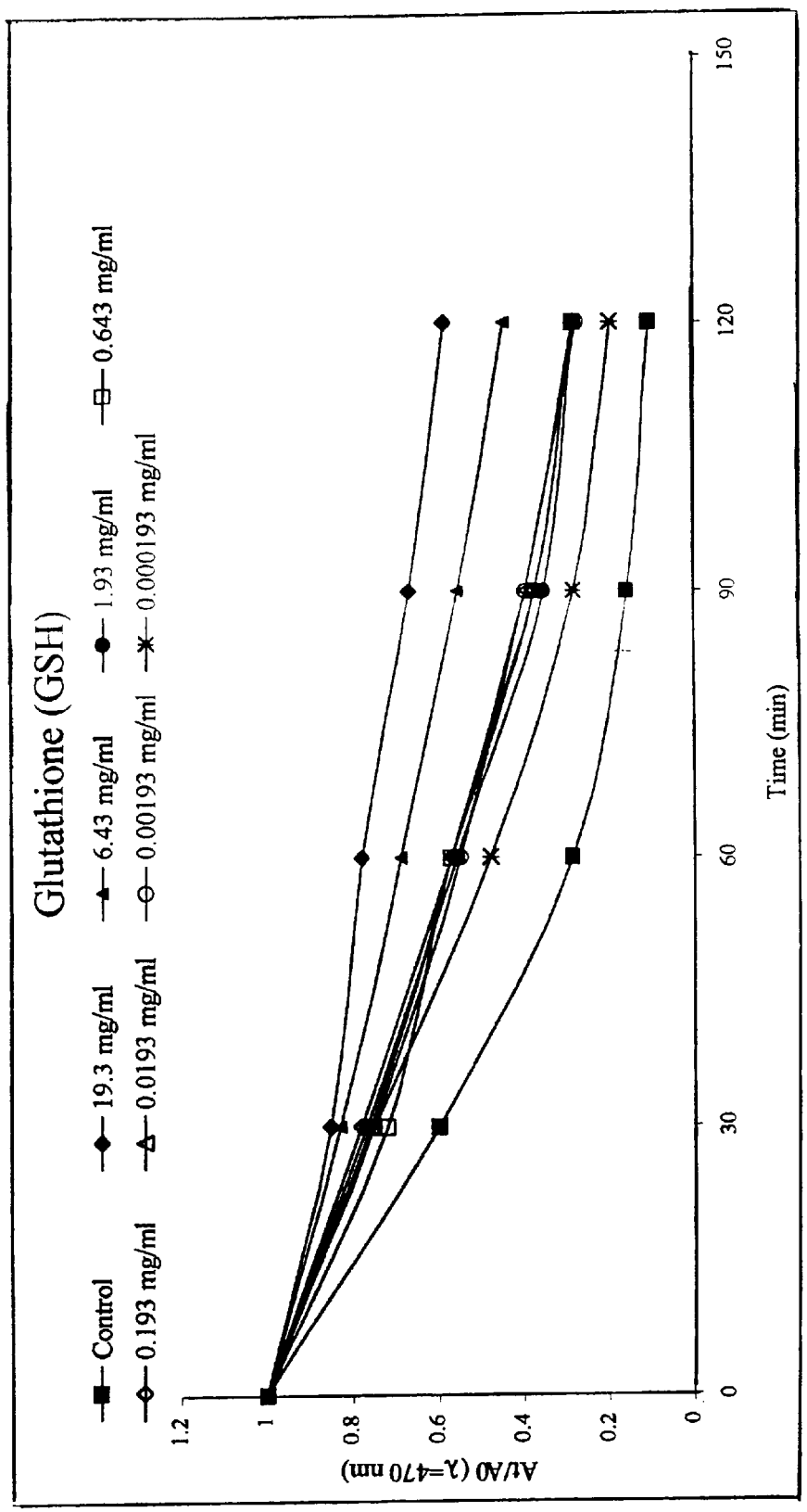

FIG. 22 Describes the results of dose response study of antioxidant activity measured in the beta-carotene test in vitro, for glutathione (GSH).

Figure 23:
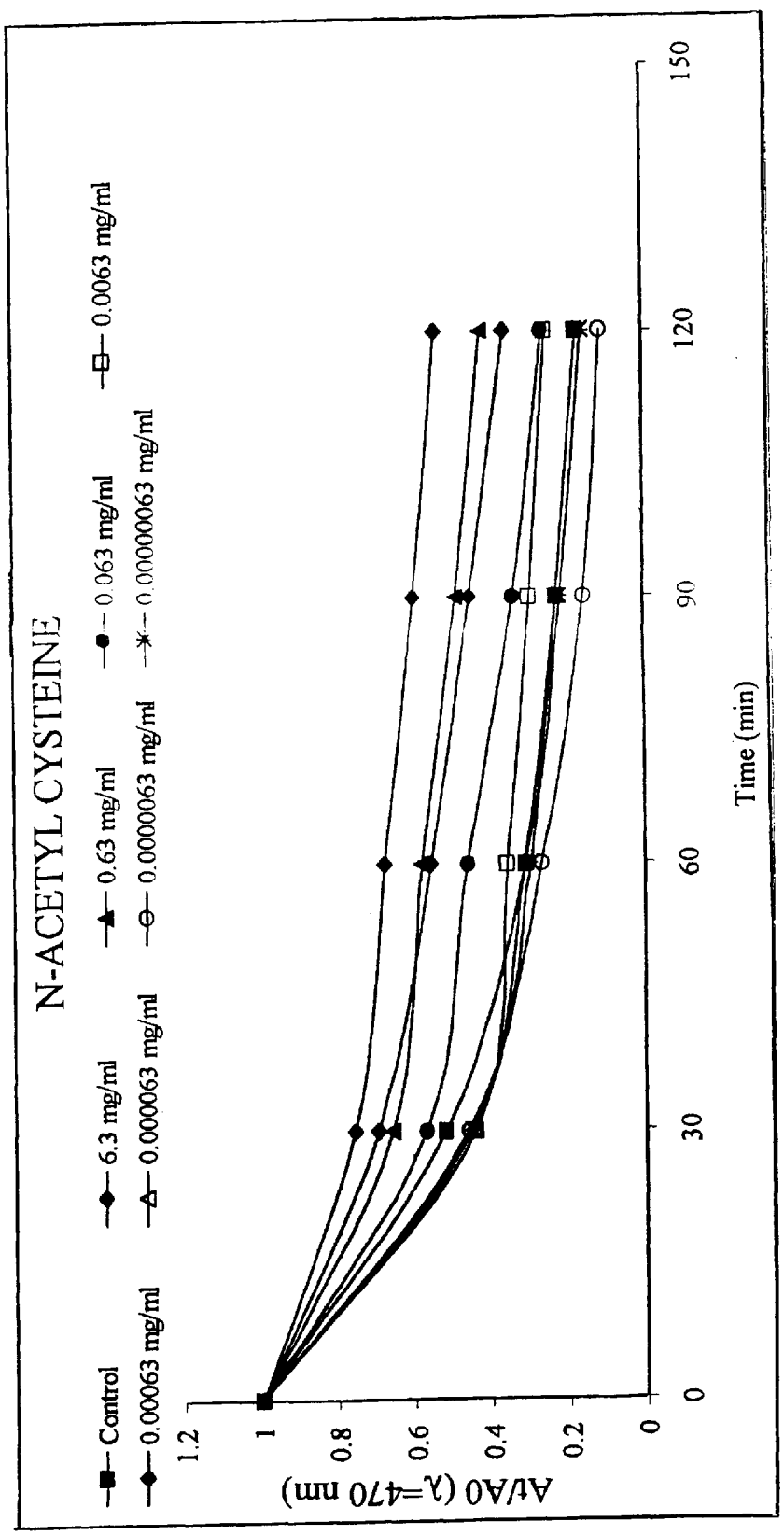

FIG. 23 Describes the results of dose response study of antioxidant activity measured in the beta-carotene test in vitro, for N-acetyl cysteine (NAC).

Figure 24:
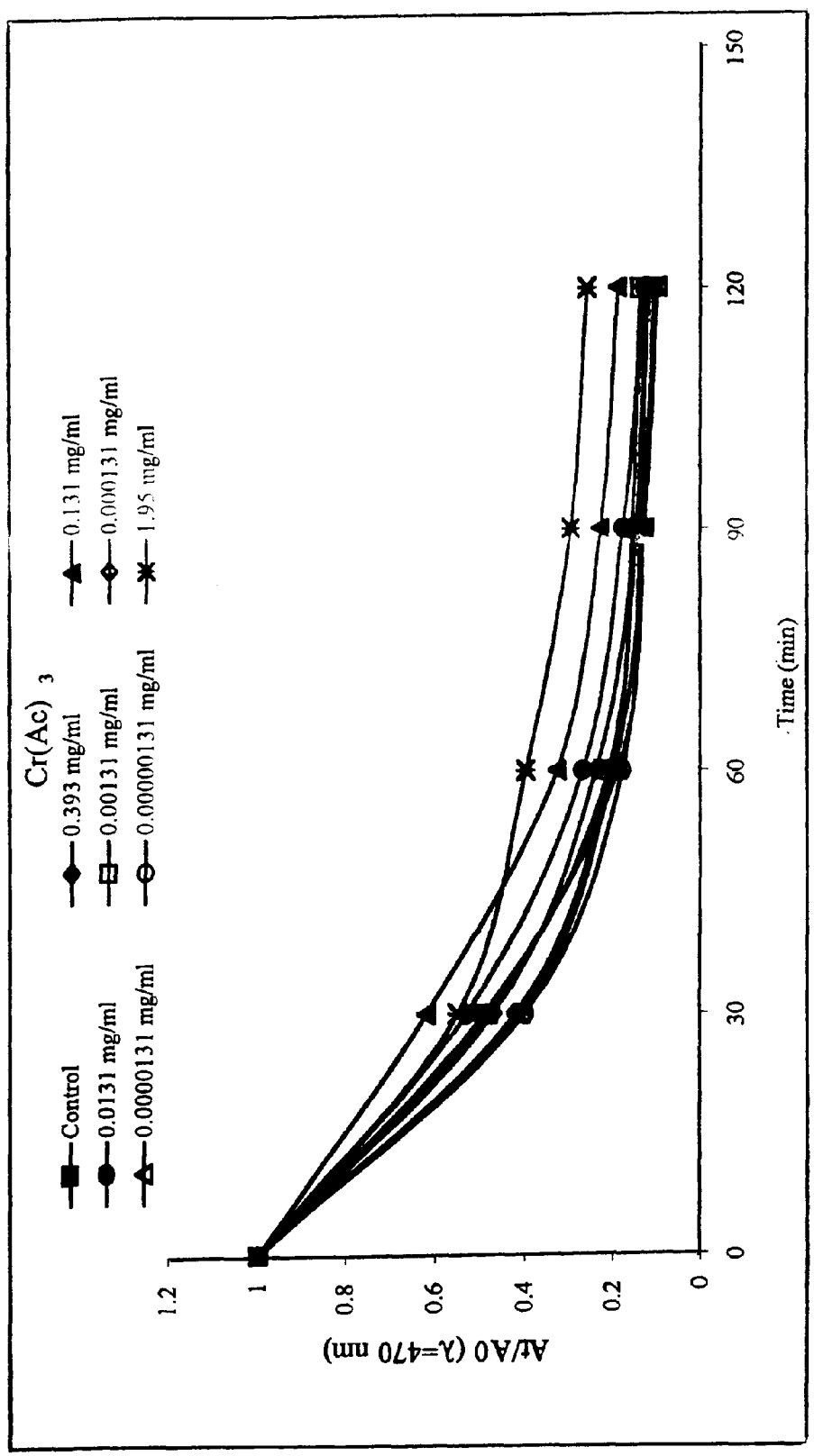

FIG. 24 Describes the results of dose response study of antioxidant activity measured in the beta-carotene test in vitro, for chromium acetate (Cr-acetate). (concentrations written according to chromium concentrations in the compound).

Figure 25:
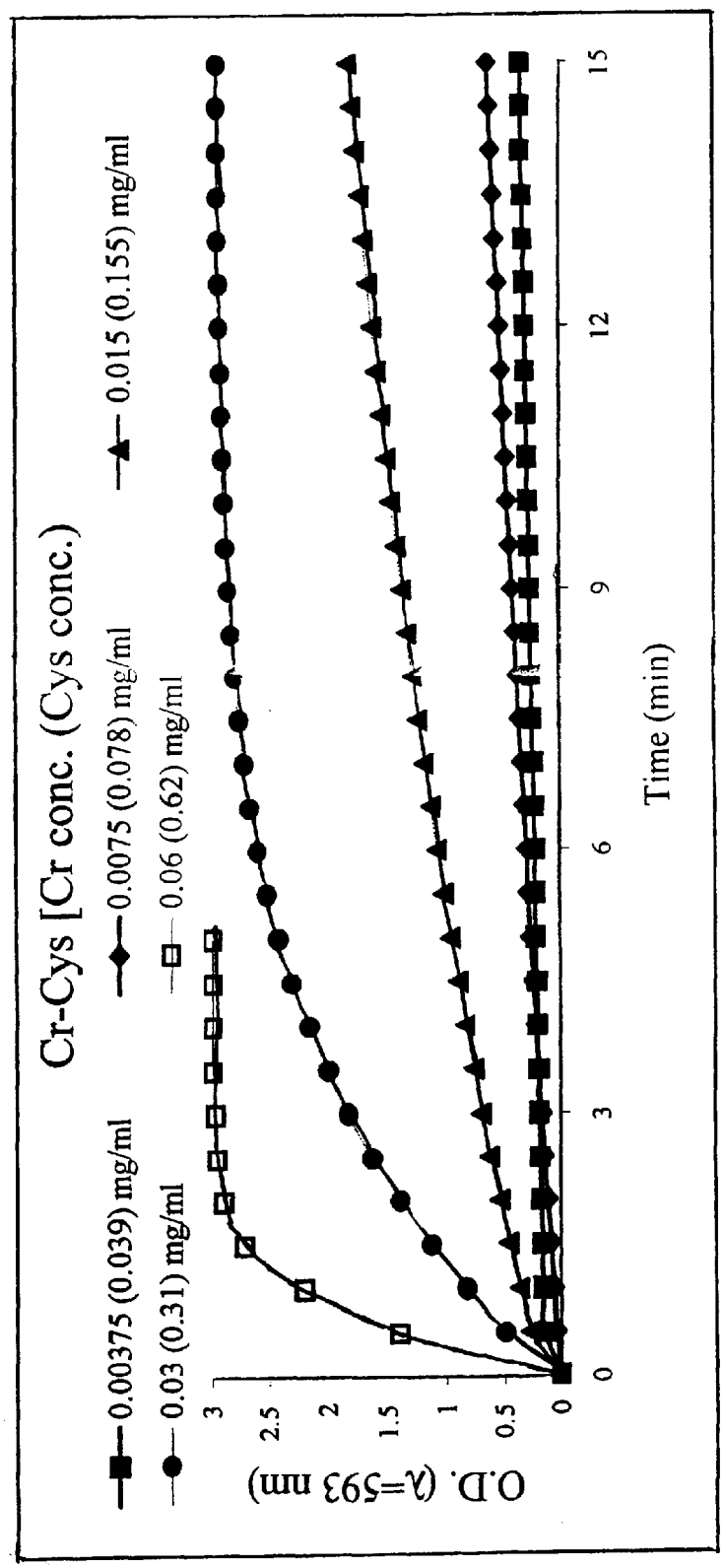

FIG. 25 describes dose dependent antioxidant activity measured in the FRAP assay in vitro, for Cr-Cys complex. (The concentrations in parenthesis relate to Cysteine concentrations in the sample).

Figure 26:
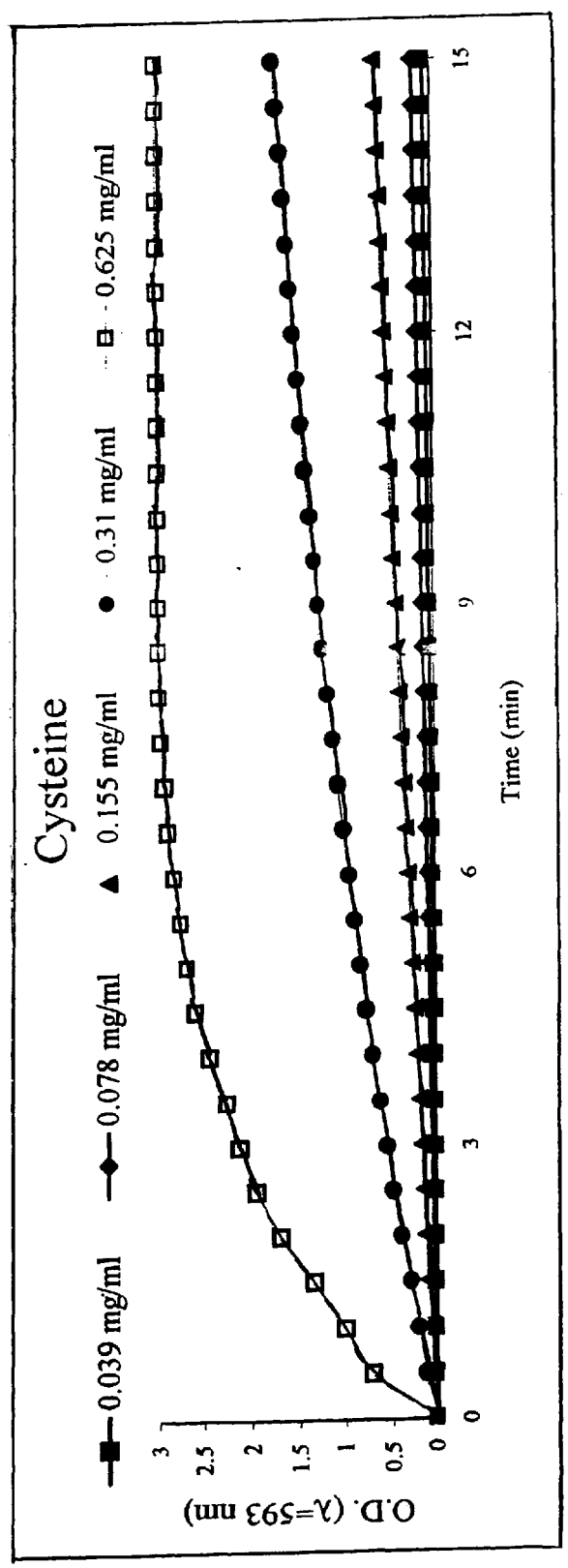

FIG. 26 describes dose dependent antioxidant activity measured in the FRAP assay in vitro, for Cysteine.

Figure 27:
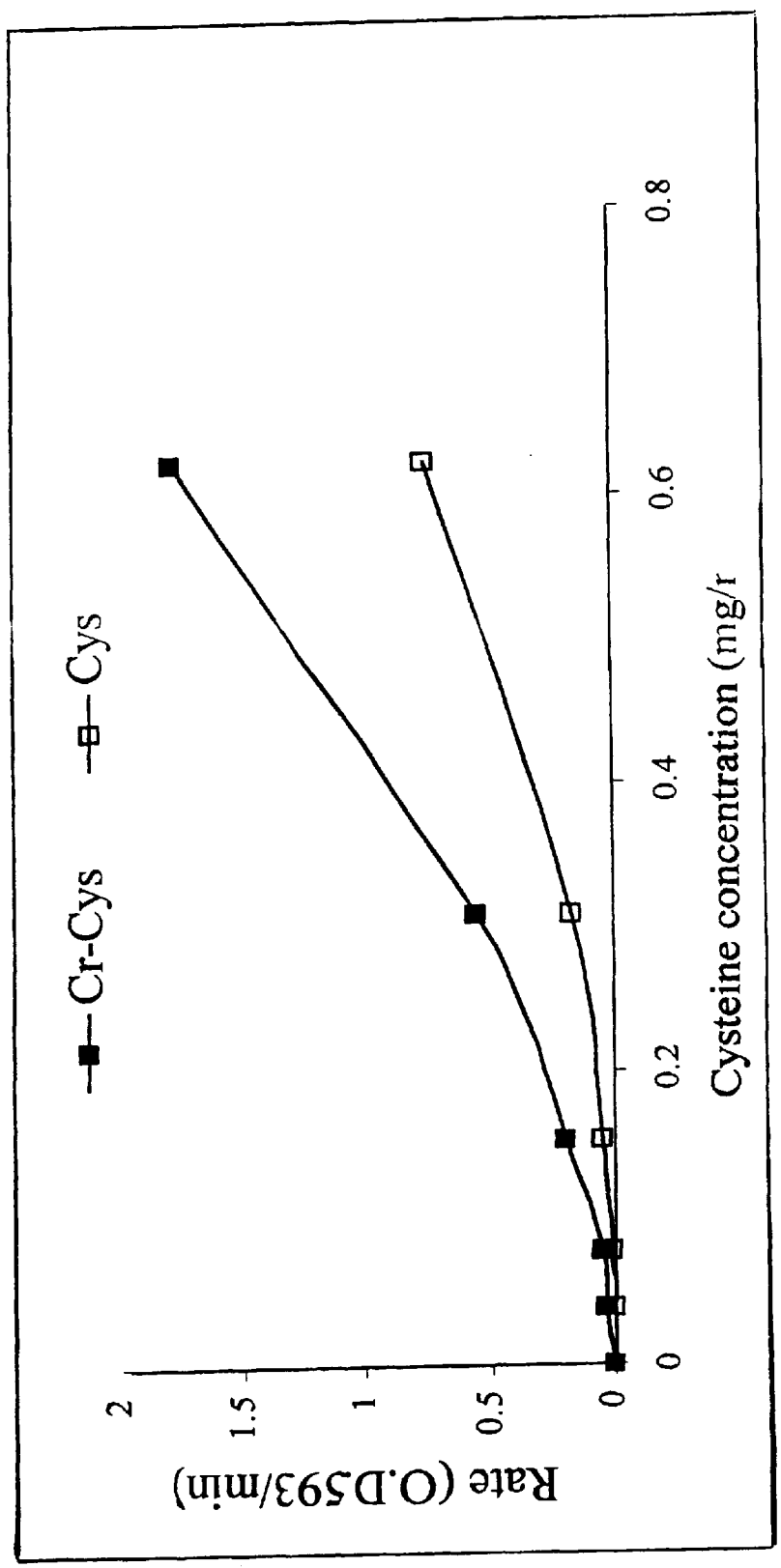

FIG. 27 describes the results of the dose response studies of antioxidant activity measured in the FRAP assay in vitro, for Cr-Cys complex and the strating material Cysteine.

4. DETAILED DESCRIPTION OF THE INVENTION

The present invention generally pertains to reveal processes, formulations and methods for use of natural compositions, with or without chromium containing compounds, from a variety of natural sources including, but not limited to, a yeast strain *S. carlsbergensis, S. cerevisiae* or a saltbush *Atriplex halimus,* growing in the Mediterranean area. The present invention is also directed to processes of making, formulations and methods for use of synthetic chromium compositions. The methods are directed to regulate abnormalities related to oxygen radicals, lipid peroxidative, cell proliferative diseases and/or vascular diseases, diabetes and diabetic complications. The present invention also provides formulations and methods for inducing cellular and biochemical changes in cells and tissues that show functional deficit in diseases including cancer, cardiovascular disease, cell proliferative diseases and/or vascular diseases, diabetes, obesity, and in preventing damage of cells and tissues by oxygenated free radials.

A free radical is a molecule with an odd, unpaired electron which makes the molecule unstable and highly reactive. Small amounts of these compounds are produced endogenously by the mitochondria electron transport system and endoplasmic reticulum in microsomes and peroxisomes. Oxygen free radicals, the superoxide anion, the hydroxyl radical and their intermediary, hydrogen peroxide, are believed to be generated during ischemia, reperfusion tissue damage, necrosis, inflammation or aging. These free radicals interact with other cellular constituents such as lipids and deoxyribonucleic acid with subsequent formation of multiple degradation products. Lipid peroxidation forms lipid peroxides and aldehydes that interact with protein sulfhydryl groups perpetuating cellular damage.

Normally, protective mechanisms are present in the cell to prevent damage by free radicals. For example, the primary mechanism of clearance of superoxide anion from biological systems is superoxide dismutase, which catalyzes the dismutation of the superoxide anion to hydrogen peroxide and oxygen. The cytoplasmic enzymes glutathione peroxidase and catalase provide the final detoxification steps with the reduction of hydrogen peroxide to oxygen. Fridovich, I., 1983, Annu. Rev. Pharmacol. Toxicol. 23: 239–257.

4.1 Cardiovascular Disease

Cardiovascular disease, including myocardial infarction and stroke is the major cause of death in Western society, accounting for more than 50% of all the deaths in the United States. A number of risk factors have been identified including smoking, high blood pressure, elevated cholesterol, stress, lack of exercise or elevated triglycerides. Attention has begun to focus on increased intakes of protective factors such as Vitamin E, rather than decreased intakes of causative and contributory agents.

Oxidized low-density lipoprotein cholesterol (O-LDL) is a major contributory factor in the initiation of atherosclerosis. O-LDL initiates several reactions that eventually lead to the formation of atherosclerotic plaques. The formation of O-LDL may be controlled by antioxidant nutrients, for example butylated hydroxytoluene, beta-carotene, vitamin E and vitamin C.

Smoking, a major risk factor for heart disease, contains compounds such as inorganic radicals, organic radicals and hydrogen peroxide, all of which are capable of oxidative damage and of depleting the body's pool of antioxidant nutrients.

Abnormal platelet aggregation occurs when platelets are unusually sticky, and can lead to abnormal blood clotting and blood vessel occlusion. Platelet aggregation is influenced by prostaglandins, specifically thromboxane, which signal the platelets to adhere to the blood vessel wall.

Thus, the natural and synthetic antioxidants of the present invention which inhibit production of lipid peroxides and oxidation of LDL, modulate arachidonic acid metabolism by inhibiting cyclooxygenase 2 (COX-2) and exhibit antioxidant, anti-inflammatory and antiplatelet activities, provide novel products and methods for treatment of vascular and proliferative diseases.

The natural and synthetic compositions of the present invention have a role in preventing development of atherosclerosis and treatment of cardiovascular disease as shown in Section 6 below, by the ability of these compounds to protect the cells from oxidant damage in vitro.

The natural and synthetic compositions of the present invention also have a role in cardiac bypass surgery by preventing the oxidative reperfusion injury that can occur during bypass surgery.

4.2 Cancer

Cancer is responsible for about 20% of deaths in the United States and it is well recognized that the majority of cancer cases are ascribable to environmental factors, for example, chemicals, radiation and viruses. The most important sources for man would appear to be chemicals in tobacco smoke and the diet. Exposure to ultra-violet radiation is responsible for the increasing rates of skin cancer.

The mechanisms by which carcinogenesis proceeds, eventually resulting in the growth of detectable malignant tumor in a person, is through radical generation and radical-mediated reactions. Vitamins C and E and Selenium, are antioxidants, and as such, have been examined for their capacities to inhibit carcinogenesis and development of malignant tumors. Less extensive data on the interactions of other trace elements with carcinogenesis are available. There is an inverse association between food processing and chromium content in foods in the United States. The importance of dietary chromium complexes and this association within the United States where there is a great deal of food processing had not been heretofore evaluated. Therefore, the natural antioxidants, with and without chromium and synthetic antioxidant chromium complexes of the present invention, are useful in inhibiting free radial production, and free radical-mediated carcinogenesis and malignant tumor formation.

It was found that a mixture of antioxidants (beta carotene, vitamin E, vitamin C and reduced glutathione) is much more effective in preventing carcinogenesis in in vivo cancer models, than each of the individual components. [G. Shklar et al. Nutrition and Cancer, p 145, 1993]. Thus, the natural and synthetic compositions of the present invention, may serve as antioxidants by using them alone or in combination with other antioxidants.

4.5 Diabetes Mellitus

Diabetes mellitus is a syndrome initially characterized by a loss of glucose homeostasis. The disease is progressive and is associated with high risk of atherosclerosis, kidney and nerve damage as well as blindness. Abnormalities in the regulation of peroxides are postulated to result in establishment of the disease and its longer term complications.

Diabetes mellitus is a complex syndrome involving severe insulin dysfunction along with gross abnormalities in glucose homeostasis and lipid metabolism. The disease is generally divided into two major groups Insulin Dependent Diabetes Mellitus (IDDM, or type I), and Non Insulin Dependent Diabetes Mellitus (NIDDM, or type II). In IDDM there is a total or near total loss of insulin secretion, whereas in NIDDM there is resistance to insulin effects. Both forms are equally devastating with respect to their later complications. The diabetic patient has a 25-fold increase in the risk of blindness, a 20-fold increase in the risk of renal failure, a 20-fold increase in the risk of amputation as a result of gangrene and a 2 to 6-fold in the risk of coronary heart disease and ischaemic brain damage. In general life expectancy for a diabetic individual is decreased by third.

Oxygen free radicals (OFRs) have been implicated in the pathogenesis of diabetes mellitus. Hyperglycemia causes increased production of OFRs through auto oxidation of glucose and also by non enzymatic protein glycation. OFRs exert their cytotoxic effects on membrane phospholipids resulting in the formation of malondialdehyde (MDA). Antioxidant enzymes (catalase, glutathione peroxidase and superoxide dismutase) offer protection against oxidative injury. Increased levels of OFRs could be due to their increased production and/or decreased destruction. It was shown that the activity of the antioxidants systems is decreased in diabetic individuals. Plasma levels of ascorbic acid and platelet vitamin E levels are decreased in diabetes. Thus excess consumption of antioxidants may reduce an endogenous oxidative stress.

In diabetes, significant changes in lipid metabolism occur, leading to vascular complications. Oxidation of lipids in plasma lipoproteins and in cellular membrane is associated with the development of vascular disease in diabetes. Diabetes and hyperlipidemia alone are not sufficient to induce vascular disease, but oxidative stress may be an independent risk factor in the development of vascular disease. Metabolic stress resulting from changes in status of antioxidant defense systems could lead to oxidative stress in diabetes. There is evidence of alterations in free radical metabolism in various diabetic tissues. Lipid peroxide levels in diabetic plasma are significantly higher than in healthy individuals. Low density lipoprotein has been reported to be more prone to oxidation in diabetes. [R. Kakkar et al., Mol. Cell. Biochem. 151: 113–119, 1995], [S. P. Wolff, Brit. Med. Bull. 49 (3): 642–652, 1993].

The natural and synthetic antioxidants of the present invention are useful to inhibit free radical production, and by doing so, decrease the oxidative damage caused to diabetic tissues.

The present invention provides a method comprising administering to a patient in need, a composition of the invention containing natural compositions with or without chromium and synthetic chromium complexes, in sufficient amounts, to inhibit oxygen free radical production and lipid peroxidation associated with it. The present invention also provides compositions comprising complexes formed with magnesium, manganese, zinc, molybdenum, boron and mixtures thereof, instead of chromium.

4.5 Inflammatory Diseases, Cell Proliferative Diseases and Aging

The prevalence of arthritis and other rheumatic conditions in the United States is about 15 percent, and it is projected to rise when the greater proportion of the population will reach an advanced age. Rheumatoid arthritis may begin as early as infancy, but onset usually occurs in the fifth or sixth decade, being more prevalent in women than in men. No specific diet or climate will alter the course of rheumatoid arthritis. Besides conveying an understanding of the disease, management involves efforts to relieve pain and discomfort, to preserve strength and joint function and to attend to systemic complications. Drugs are used in several ways as analgesics, as anti-inflammatory agents and for immunosuppressive effects. Aspirin and newer non-steroidal anti-inflammatory drugs (NSAIDs) are used for treatment. All currently available NSAIDs nonselectively block both the cyclooxygenases 1 and 2. However, a significant number of patients do not experience satisfactory symptomatic relief with a disease modifying single anti-rheumatic drug. The natural and synthetic compositions of the present invention are useful in relieving symptomatic pain and in exerting antioxidant effects in rheumatoid arthritic patients.

Injury to different types of cells, for example structural injury to endothelial cells or chemical injury to skin cells by ultra-violet radiation, generally results in release of oxygen free radicals, alteration in permeability and infiltration by cells of the immune system. The natural and synthetic compositions of the present invention are useful in inhibiting free radical formation, and thus preventing damages that may occur in skin cell or endothelial cells.

4.6 Obesity

Thirty three percent of adults over the age of 20 in the United States are obese. Obesity is loosely defined as an excess of fat over that needed to maintain health. Many factors are involved in the pathogenesis of obesity, including the control of feeding behavior, mechanisms of fat storage, the components of energy intake and expenditure, and genetic and psychological influences. Surplus nutrients are converted to triglycerides and stored in adipocytes. The storage is regulated by the enzyme lipoprotein lipase. The lipoprotein lipase activity varies in different parts of the body and fat deposits in the highly active sites are associated with higher cholesterol levels and other cardiac risks. The natural and synthetic compositions of the present invention are useful in regulating obesity by regulating functions including, but not limited to, reducing cholesterol levels, regulating lipoprotein lipase activity and triglyceride synthesis and exerting antioxidant effects in obesity.

4.7 Formulations and Dosage

Chromium containing natural and synthetic compositions may be formulated into pharmaceutical preparations for administration to animals for a variety of effects including, but not limited to, glucose regulation, triglyceride and fatty acid regulation, lipid peroxide production and arachidonic acid metabolism regulation, cardiovascular diseases, diabetes, inflammatory diseases, eczema, skin warts, psoriasis or arthropathy.

The natural and synthetic compounds may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations maybe in unit dose or multi-dose sealed contains.

Dosages for oral administration of chromium containing natural and synthetic compositions range from 50 to 500 microgram Cr/day, commonly 50 to 250 microgram Cr/day, and typically from 50 to 100 microgram Cr/day. Dosage for natural antioxidants with or without chromium range from 0.2 gram to 2 gram extract /day for human use.

Dosage amount and interval may be adjusted individually to provide plasma levels of the active moiety which are sufficient to maintain the antioxidant and other metabolic effects.

Alternatively, one may administer the compound in a local, rather than oral manner, for example, via injection of the compound directly into the target site, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Example of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system for example, in a liposome coated with a tissue specific antibody. The liposomes will be directed to and taken up selectively by the target tissue.

In cases of local administration or selective uptake, the effective local concentration of the chromium compound may be related to plasma concentration.

5. EXAMPLES 5.1 Extraction, Isolation and Evaluation of Natural Antioxidants from Saltbush Powdered dried leaves (90 g) of saltbush were refluxed in a mixture of water (150 ml), methanol (150 ml), and chloroform (150 ml) for 4 hours. The crude mixture was filtered and the solvents evaporated. The crude brown extract was dissolved in 50 ml D.D.W and fractionated using liquid-liquid extraction with the following solvents: 150 ml n-Hexane, 150 ml Chloroform and 150 ml Ethyl acetate. The process of extraction and purification is described in FIG. 1. The evaluation of the antioxidant activity in the extracted organic fractions and the remaining aqueous phase were made by using the FRAP assay. The organic and aqueous fractions were dissolved in ethanol and D.D.W respectively, for the FRAP assay.

FRAP Assay

The ferric reducing/antioxidant power (FRAP) assay is a recently developed, direct test of "total antioxidant power" [F. F. Benzie and J. J. Strain, Method in Enzymology, Vol. 299, pp: 15–27].

In contrast to other tests of total antioxidant power, the FRAP assay is simple, fast, inexpensive and robust. The FRAP assay uses antioxidants as reductants in a redox-linked calorimetric method.

Concept of FRAP Assay

A biological antioxidant has been defined as "any substance that, when present at low concentrations compared to those of an oxidizable substrate, significantly delays or prevents the oxidation of that substrate. However, unless an antioxidant prevents the generation of an oxidizing species, for example, by metal chelation or enzyme-catalyzed removal of a potential oxidant, a redox reaction still generally occurs, even in the presence of an antioxidant. The difference is that the oxidizing species reacts with the antioxidant instead of the "substrate', i.e., the antioxidant reduces the oxidant. In simple terms, electron-donating antioxidants can be described as reductants, and inactivation of oxidants by reductants can be described as redox reactions in which one reactive species is reduced while another is oxidized. In this context, therefore, "total antioxidant power" may be referred as "total reducing power".

The FRAP assay can be performed on a wide range of complex biological fluids, including plasma, serum, saliva, tears, urine, cerebrospinal fluids, exudates, transudates and aqueous and ethanolic extracts of drugs, foods and plants, as well as on simple and heterogeneous solutions of pure antioxidants.

Principle of FRAP Assay

At low pH, measuring the change in absorption at 593 nm can monitor reduction of a ferric tripyridyltriazine (FeIII-TPTZ) complex to the ferrous form, which has an intense blue color. The change in absorbance is directly related to the combined or "total" reducing power of the electron-donating antioxidants present in the reaction mixture.

Materials and Methods

The working reagent is prepared by mixing 300 mM acetate buffer, pH 3.6, 10 mM TPTZ (2,4,6-tripyridyl-s-triazine) in 40 mM HCl and 20 mM $FeCl_3.6H_2O$ in the ratio of 10:1:1. One milliliter of working reagent is mixed with 100 µl of the test sample and the absorbance at 593 nm is read, for 15 minutes at 30 seconds intervals. The results are computing in a graph of absorbance vs. time and the antioxidant power was calculated from the rate (slope of the linear line) in the graph. The antioxidant activity of the fractions extracted from the saltbush was measured. The highest activity was in the fraction extracted with chloroform. (Table 1, FIG. 2).

TABLE 1

Antioxidant activity of fractions extracted from saltbush by several solvents. "Crude" refers to product obtained after reflux, filtration of debris and evaporation of solvents.

| Extraction solvent | Weight (g) | Rate ($\Delta A_{593}$/min) at 0.5mg/ml |
|---|---|---|
| crude | 4.0 | 1.096 |
| Hexane | 0.680 | 5.864 |
| Chloroform | 0.117 | 9.956 |
| Ethyl acetate | 0.065 | 8.344 |
| water | 2.5 | 1.032 |

5.1.1 Aqueous Antioxidants

The aqueous phase was further purified by filtration through molecular ultrafiltration membranes (Spectrum), of molecular weight cut off 3000 and 1000 Dalton. The antioxidant activity of the different fractions is presented in Table 2 & FIG. 3, indicating higher rate of activity for the fraction between 1000–3000 Dalton.

TABLE 2

Antioxidant activity of aqueous fraction separated through size exclusion membranes

| Molecular size | Weight (g) | Rate ($\Delta A_{593}$/min) at 0.5 mg/ml | Enhancement Degree* |
|---|---|---|---|
| crude |  | 1.08 |  |
| >3000 | 0.054 | 1.120 | 1.04 |
| <3000 | 2.4 | 0.964 | 0.89 |
| <1000 | 1.3 | 0.300 | 0.28 |
| 1000–3000 | 1.0 | 2.552 | 2.36 |

*Enhancement degree: The rate of antioxidant activity of the examined fraction divided by the rate measured for the crude extract The active fraction (1000–3000 Dalton) was further purified by size exclusion column, Sephadex G-25. 0.88 g were loaded on the column (21×3 cm), and 10 ml fractions were collected by washing the column with 380 ml double distilled water. The most active material was found in fraction 35, which indicates a relative low molecular weight (Table 3).

TABLE 3

Antioxidant activity of saltbush aqueous fraction chromatographed on Sephadex G-25.

| Fraction number | Weight (g) | Rate ($\Delta A_{593}$/min) at 0.25 mg/ml | Enhancement Degree* |
|---|---|---|---|
| crude | | 0.556 | |
| 1–28 | 880 | <5.0 | |
| 29 | 11 | 6.464 | 11.63 |
| 30 | 10 | 6.816 | 12.26 |
| 31 | 8 | 6.792 | 12.22 |
| 32 | 5 | 8.528 | 15.34 |
| 33 | 5 | 7.692 | 13.83 |
| 34 | 3 | 9.748 | 17.53 |
| 35 | 2 | 11.184 | 20.12 |
| 36 | 8 | 10.948 | 19.69 |
| 37 | 2 | 9.104 | 16.37 |

The most active fractions were combined and further purified on a G-15 column, followed by silica gel column, to yield the active fraction presented in Table 4, FIG. 4.

TABLE 4

Antioxidant activity of saltbush aqueous fraction chromatographed on Sephadex G-25 Sephadex G-15 and silica gel.

| concentration | Rate ($\Delta A_{593}$/min) |
|---|---|
| 0.0312 | 3.60 |
| 0.0625 | 7.57 |
| 0.125 | 11.28 |

FIG. 5 presents the relative increase in antioxidant activity of the active fractions recovered from several purification steps of saltbush extract. The relative increase in antioxidant activity in of the fraction purified on G-25, G-15 and silica gel columns, is 40.95 fold higher compared with the push extract. The activity of the aqueous fraction was further examined in the β carotene assay.

β-carotene Test

Evaluation of antioxidant activity is based on coupled oxidation of β-carotene and linoleic acid. The technique consists of measuring the consumption of β-carotene as a result of its oxidation process in the reaction mixture. The β-carotene-linoleic acid method has been reported as an efficient technique to detect and evaluate antioxidants from plants and from other sources by several investigation groups. Ten milligram of β-carotene were dissolved in 10 ml chloroform and 0.6 ml of the solution was added to a round flask that contained 20 mg of linoleic acid and 200 mg of Tween 20. Chloroform was removed by evaporation, and 50 ml of distilled water were slowly added to the flask with vigorous agitation to form an emulsion. Two milliliters of the emulsion were added to 1 ml of the examined antioxidant solution. The tubes were placed in a water bath at 50° C. and absorbance measurements were made at 30 minutes intervals [M. S. Taga et al., J. Am. Oil Chem. Soc. 61: 928–931, 1984].

The aqueous fraction isolated from saltbush and eluted from G25 was examined in the beta carotene assay (FIG. 6) The antioxidant activity of the above fraction was compared with the activity measured for the crude extract (FIG. 7). A dose response curve (FIG. 8) compares the relative activity of the crude extract with the active fraction eluted from G25 (the area under curve was calculated from FIG. 6 and FIG. 7 showing an increase in antioxidant activity for the more purified fraction.

5.1.2 Partial Purification of the Organic Phase

The organic fractions were chromatographed using silica gel columns. Two active fractions were isolated from ethyl acetate extract, 1 and 2, which were eluted using acetone and ethanol respectively. The Chloroform extract, was separated into two active fractions, 3 and 4, which were eluted using dichloromethane and chloroform/methanol 20/1 respectively, as shown in Table 5 & FIG. 9.

TABLE 5

Antioxidant activity of fractions extracted from saltbush by several organic solvents and chromatographed on silica gel column

| Fraction number | Extraction solvent | Weight (mg) | Rate ($\Delta A_{593}$/min) at 0.25 mg/ml | Enhancement |
|---|---|---|---|---|
| crude | | | 0.556 | |
| 1 | Ethyl acetate | 15 | 6.340 | 11.4 |
| 2 | Ethyl acetate | 24 | 5.236 | 9.42 |
| 3 | Chloroform | 15 | 8.416 | 15.14 |
| 4 | Chloroform | 9 | 7.876 | 14.17 |

5.2 Extraction and Isolation of Natural Antioxidants from Yeast 5.2.1 Aqueous Antioxidants 20 grams of yeast were dissolved in 100 ml of water. Disruption of cell wall was performed either mechanically by using a bead mill (Braun) or by autolysis by incubating yeast cells for several days in a diluted $NH_4OH$ solution at 50° C. Alternatively, a commercial yeast extract can be used. To 20 grams of yeast extract in 100 ml water an equal volume of Butanol was added and the suspension was refluxed for 3 hours at 50° C. Trace amounts of Butanol were removed by evaporation under vacuum. The water phase was separated and ultrafiltrated using a membrane of 3000 CO. The filtrate was loaded on DEAE cellulose column and the water flow through was collected.

The antioxidant activity of the aqueous fraction extracted from yeast, was measured in the beta carotene test in solution containing linoleic acid. Beta carotene linoleic acid emulsion was incubated in the absence (control), or presence of different concentrations of the active extract. Changes in beta carotene absorption at 470 nm were measured (FIG. 10). Dose dependent activity of the antioxidant aqueous fraction from yeast is presented in FIG. 11. Area under curve represents the relative activity of each concentration of the aqueous fraction calculated according to FIG. 10.

5.2.2 Organic Antioxidants

Fifty grams of granulated yeast extract were dissolved in 100 ml distilled water by stirring for 30 min. An equal volume of methanol and 2 volumes of chloroform were added, and sequentially mixed with the yeast extract suspension. The lower chloroform phase was separated from the upper aqueous phase. The chloroform phase was taken for subsequent examination. There is a relative high antioxidant activity in the chloroform fraction extracted from yeast. The antioxidant activity of the crude yeast extract in the FRAP assay is presented in FIG. 12. Much higher activity was achieved for the chloroform fraction as shown in FIG. 13.

Dose response curve for the antioxidant activity in the crude extract and the chloroform fraction is presented in FIG. 14, showing much higher antioxidant rate for the fraction extracted with chloroform.

5.3 Synthetic Chromium Containing Compositions with Antioxidant Activity

The method of synthesis of three members of the chromium family of complexes is described below:

Chromium Cysteine (Cr-Cys)

One gram (3.7 mmole) of chromium chloride ($CrCl_3$) was dissolved in 40 ml of deionized water to get a green solution. 2 g (15 mmole) of cysteine (Cys) was dissolved in 40 ml of deionized water were added, and the reaction mixture was stirred for 2 hours at 40° C. until the solution turned violet. The absorbance peaks for Cr-Cys are 410 and 550 nm. The absorbance peaks for $CrCl_3$ are 440 and 630 nm. Cr-Cys is strongly bound to the cation exchange column Dowex 50×8.

Chromium-Glutathione (Cr-GSH)

One gram (3.7 mmole) of chromium chloride ($CrCl_3$) was dissolved in 40 ml of deionized water to get a green solution. 4.6 g (15 mmole) of glutathione (GSH) dissolved in 40 ml of deionized water were added, the pH of the reaction mixture adjusted to 6, and the reaction mixture was stirred for 3 hours at 40° C. until the solution turned violet. The absorbance peaks for Cr-GSH are 410 and 550 nm.

Chromium N-Acetyl Cysteine (Cr-NAC)

Half a gram (1.85 mmole) of chromium chloride ($CrCl_3$) was dissolved in 30 ml of deionized water to get a green solution. 1.5 g (9.2 mmole) of N-acetyl cysteine (NAC) dissolved in 40 ml of deionized water were added, and the mixture was stirred for 3 hours at 40° C. until the solution turned dark green-blue. The absorbance peaks for Cr-NAC are 425 and 575 nm. Cr-NAC is a cationic complex and binds to the cation exchange column Dowex 50×8.

Chromium complexes: Cr-cysteine, Cr-Glutathione and Cr-NAC exhibit a dose dependent antioxidant activity in β Carotene test (FIGS. 15,16,17 respectively). The reactants $CRcl_3$ (FIG. 18), or $Cr2(SO4)_3$ (FIG. 19), have relatively much lower antioxidant effect. FIG. 20 and Table 6 demonstrate the relative antioxidant activity for chromium complexes (Cr-Cys, Cr-Glut, and Cr-NAC) and their reactant CrCl3. While EC50 for CrCl3 lies around 7×10−4 mg Cr/ml, EC50 for both Cr-GSH and Cr-NAC—are around 8—10−7 mg Cr/ml, and for Cr-Cys, the most active complex—8×10−8 mg Cr/ml.

Results obtained indicate that the reactants like Cysteine, Glutathione, NAC, (or $CrCl_3$ as indicated above) have either no antioxidant activity, (Cysteine, FIG. 21), or lower activity (Glutathione, FIG. 22, and NAC, FIG. 23), than the chromium complexes of the respective compounds (FIGS. 15, 16, 17). Cr Acetate, being a basic chromium acetate complex, rather than a simple chromium salt, lacks any antioxidant activity (FIG. 24).

Chromium-Cystine which is synthesized similarly to Chromium-Cysteine did not show any antioxidant activity.

TABLE 6

$EC_{50}$ for antioxidant activity of chromium compounds in β Carotene test:

| Chromium Compound | $EC_{50}$ (mg Cr/ml) |
|---|---|
| $CrCl_3$ | $7.2 \times 10^{-4}$ |
| Cr-NAC | $2.7 \times 10^{-7}$ |
| Cr-GSH | $2.7 \times 10^{-7}$ |
| Cr-Cys | $7.8 \times 10^{-8}$ |

The antioxidant activity of Cr-Cys, the most active chromium complex in the beta carotene assay, was examined also in the FRAP assay. The activity of Cr-Cys was compared to those of the starting materials, cysteine and $CrCl_3$.

FIG. 25 presents the change in absorbance at 593 nm, for different concentrations of chromium in the "Cr-Cys" complex (the concentrations in parenthesis relate to cysteine concentration in the same samples). FIG. [26] presents the change in absorbance at 593 nm for different concentrations of cysteine (comparable concentrations of cysteine as in FIG. 25, were used). The starting material, $CrCl_3$ was found inactive in the FRAP assay, at all concentrations used.

FIG. 27 summarizes the rate, calculated from FIGS. 25 and 26, as a function of the concentration of cysteine in the reaction mixture of Cr-Cys and in pure Cysteine solutions. Cr-Cys was 2.5-fold more active than cysteine (at equal concentrations of cysteine), indicating that the complex formed from chromium and cysteine has a higher antioxidant activity than the starting material, cysteine.

5.4 In vivo Reduction of Lipid Peroxidation by Natural Composition Extracted from Yeast One of the most devastating effects of Oxygen Free Radicals (OFRs), in the organism is the oxidation of lipids, resulting in the formation of Malondialdehydes (MDAs). The level of lipid peroxidation can be assessed by measuring the level of thiobarbituric acid reactive substances (TBARS) in tissues of diabetic animals. MDAs react with thiobarbituric acid to form a colored substance which can be measured calorimetrically according to the method of K. Prasad et al., Mol. Cell. Biochem. 115: 49–58, 1992.

Diabetes was induced by sub cutaneous injection of Streptozotocin (60 mg/Kg body weight). Diabetic animals were divided to two groups: those who were treated with the active extract from yeast and those who were left untreated as diabetic control. In addition, another group of healthy animals was used as healthy control. The treated diabetic animals were orally administered with 10 daily doses of the active fraction isolated from yeast extract (0.5 gr/animal). The level of TBARS in the hearts of the three different groups was determined ("Non induced" values). In addition, the concentration of lipid peroxidation induced by ferrous sulfate in the hearts of the different groups, was also measured ("Induced" values).

TABLE 7

TBARS concentration in hearts of diabetic rats treated with antioxidant fraction from yeast (values in nM/gr tissue)

| | Healthy control | Diabetic untreated | Diabetic treated with Antioxidant fraction |
|---|---|---|---|
| Non induced | 11.82 ± 1.8 | 85.4 ± 11.5 | 60.9 ± 7.5 |
| Induced | 17.7 ± 3.6 | 122.4 ± 20.2 | 90.9 ± 14.5 |

The values of both induced and non induced and non induced lipid peroxides is much higher in diabetic rats compared with healthy controls. There is a remarkable decrease in the level of lipid peroxides in the animals treated with the antioxidant extract derived from yeast, indicating a beneficial effect of the antioxidant extract.

The present invention is not to be limited in scope by the embodiments disclosed in the examples which are intended as an illustration.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

What is claimed is:

1. A natural antioxidant composition with or without chromium, isolated from a yeast strain comprising of *S. carlsbergensis*.

2. The antioxidant composition according to claim 1 further comprising an antioxidant selected from the group consisting of vitamin C, vitamin E, reduced glutathione, manganese, beta-carotene, ergothioneine, zinc, selenium, cysteine, N-acetyl cysteine, methionine or 2-mercaptoethanol.

3. A purified chromium containing natural antioxidant isolated from a saltbush.

4. The antioxidant composition of claim 3 further comprising an antioxidant selected from the group consisting of vitamin C, vitamin E, reduced glutathione, manganese, beta-carotene, ergothioneine, zinc, selenium, cysteine, N-acetyl cysteine, methionine or 2-mercaptoethanol.

5. The antioxidant composition according to claim 4, said composition being suitable for administering to a human subject suffering from a condition including hyperglycemia, hypertriglyceridemia, hypercholesterolemia, peripheral vascular disease, neuropathy, inflammatory diseases, warts, cell proliferative diseases, eczema, anthropathy, psoriasis or glucose intolerance.

6. A process for producing an antioxidant complex said process comprising the steps of:

(i) reacting a metal salt with a material possessing antioxidant activity to form a reaction mixture, (ii) stirring the reaction mixture at 40° C. until a desired color is obtained, and (iii) eluting all material having an appropriate molecular weight.

7. The process according to claim 6, wherein the material possessing antioxidant activity comprises, cysteine, glutathione, glucono-lactone, N-acetyl cysteine or methionine.

8. The process according to claim 6, wherein the metal salt comprises chromium chloride, magnesium chloride, manganese chloride, zinc chloride, molybdenum chloride, or boron chloride.

9. A method for regulating free radical production, said method comprising administering an effective amount of a antioxidant composition with or without chromium, wherein the antioxidant is isolated from natural sources including yeast or saltbush.

* * * * *